(12) United States Patent
Yuasa et al.

(10) Patent No.: US 6,859,364 B2
(45) Date of Patent: Feb. 22, 2005

(54) PORTABLE INFORMATION APPLIANCE

(75) Inventors: Akiko Yuasa, Kyoto (JP); Yasuaki Tanimoto, Hyogo (JP); Chie Hirai, Osaka (JP)

(73) Assignee: Matsushita Refrigeration Company, Osaka (JP)

(*) Notice: Subject to any disclaimer, the term of this patent is extended or adjusted under 35 U.S.C. 154(b) by 149 days.

(21) Appl. No.: 10/048,934

(22) PCT Filed: Jun. 6, 2001

(86) PCT No.: PCT/JP01/04761

§ 371 (c)(1),
(2), (4) Date: May 24, 2002

(87) PCT Pub. No.: WO01/95077

PCT Pub. Date: Dec. 13, 2001

(65) Prior Publication Data

US 2003/0043541 A1 Mar. 6, 2003

(30) Foreign Application Priority Data

Jun. 6, 2000 (JP) ........................................ 2000-168896
Nov. 16, 2000 (JP) ........................................ 2000-349356
Apr. 16, 2001 (JP) ........................................ 2001-116592

(51) Int. Cl.$^7$ ................................................ G06F 1/20
(52) U.S. Cl. ...................... 361/687; 361/708; 174/15.2; 165/104.33; 62/259.2
(58) Field of Search ................................ 361/683, 685, 361/687–709; 165/80.3, 80.4, 104.33, 185; 62/259.2; 174/15.2

(56) References Cited

U.S. PATENT DOCUMENTS

| | | | |
|---|---|---|---|
| 5,478,867 A | | 12/1995 | Tabor |
| 5,510,954 A | * | 4/1996 | Wyler ........................ 361/685 |
| 6,005,768 A | * | 12/1999 | Jo ............................... 361/685 |
| 6,154,360 A | * | 11/2000 | Kaczeus et al. ............ 361/685 |
| 6,243,262 B1 | * | 6/2001 | Koo et al. ................... 361/687 |
| 6,487,073 B2 | * | 11/2002 | McCullough et al. ....... 361/687 |
| 6,514,616 B1 | * | 2/2003 | Gandi et al. ................. 361/679 |

FOREIGN PATENT DOCUMENTS

| | | |
|---|---|---|
| JP | 60-33479 | 2/1985 |
| JP | 61-36595 | 2/1986 |
| JP | 4-46348 | 7/1992 |
| JP | 5-114283 | 5/1993 |
| JP | 5-66341 | 9/1993 |
| JP | 6-281089 | 10/1994 |
| JP | 7-139690 | 5/1995 |
| JP | 8-20032 | 3/1996 |
| JP | 11-191024 | 7/1999 |
| JP | 11-202978 | 7/1999 |
| JP | 11-304083 | 11/1999 |
| JP | 2000-106495 | 4/2000 |

* cited by examiner

Primary Examiner—Lisa Lea-Edmonds
(74) Attorney, Agent, or Firm—Wenderoth, Lind & Ponack, L.L.P.

(57) ABSTRACT

A portable information device such as a notebook type computer is provided with a highly efficient thermal insulator capable of blocking transfer of heat between an internal heating component and a device enclosure, so as to reduce temperature rise on a surface of the device. The portable information device is also provided with a highly efficient thermal insulator to block transfer of heat between the heating component and an expansion unit mounting case, thereby reducing temperature rise and preventing malfunction of an external expansion unit. The information device includes the thermal insulator to separate between the internal heating component and the device enclosure, another thermal insulator to separate between the heating component and the expansion unit mounting case, and a heat sink. The thermal insulator is a vacuum thermal insulator including inorganic fiber as a core member.

25 Claims, 11 Drawing Sheets

301 (301A – 301E, 301G)
302 (302A – 302E, 302G)  305 (305A, 305B)
306
303 (303A – 303D)    304 (304A, 304B)

301F
302F  307    305
306F
303F    304

PORTABLE INFORMATION APPLIANCE

TECHNICAL FIELD

The present invention relates to a portable information device such as a notebook type computer, and more particularly to a portable information device that avoids heat generated in it from being transferred to a user, and prevents malfunction.

BACKGROUND OF THE INVENTION

When heat generated within a portable information device such as a notebook type computer of recent years is transferred to a surface of a device enclosure, and raises temperature of the surface of the device enclosure, the heat on a portion of the enclosure surface that stays in contact for a long time with a body of a user of the device gives an uncomfortable feeling to the user. Sources of the heat within the computer are mainly a CPU and power supply, and a surface temperature of the CPU, in particular, reaches such a temperature that exceeds approx. 100° C.

As the latest techniques under these circumstances, there have been proposed some techniques in that thermal insulators are used to block heat between a heating component in the device and the device enclosure.

There has been proposed, for instance, a notebook type computer of a structure including a thermal insulator for isolating between a heating component in the device and a device enclosure, a heat sink disposed to a back surface of a display unit, a heat pipe for conducting heat generated in the device to the heat sink, and an air vent, as disclosed in Japanese Patent Laid-open Publication, No.11-202978. Temperature rise on the enclosure surface can be reduced to some extent by using the technique taught in the publication, 11-202978.

However, it is necessary to increase a thickness of the thermal insulator in order to attain an effect of reducing an amount of heat transferred to the surface of the device enclosure, because the effect is small if thermal insulation property of the thermal insulator is low. On the other hand, since low-profiling and weight-reduction are desired in these days for notebook type computers, it is also necessary for the thermal insulators to be small and light weight.

Besides, the heat generated within a device may cause an adverse effect to external expansion terminals such as a random-access memory (RAM) card and a local area network (LAN) card, and leads them into malfunction.

As ordinary thermal insulators, fibrous body such as glass wool, and foam body such as polyurethane foam and the like are used. In order to improve insulating properties of these thermal insulators, however, it is necessary to increase their thicknesses. The thicknesses are therefore not suitable to a need to save or use spaces efficiently due to limitation in the spaces available for installation of the thermal insulators.

As one of the ways to solve the problem, a vacuum thermal insulator including a core member, which maintains a space, and an enveloping member, which shields the space from the open air is available. Powdery material, fibrous material, continuously-formed foam body, and the like are used generally as the core member. However, even more efficient vacuum thermal insulators are now in demand.

Thus, Japanese Patent Laid-open Publication, No.60-33479 teaches a vacuum thermal insulator characterized by uniformly-distributed powdery carbon into pearlite powder for improving efficiency of the core member. It also discloses the vacuum thermal insulator including the powdery carbon consisting of carbon black. The thermal insulation property can be improved by 20% under the optimum condition by the uniformly distributing carbon black into the pearlite.

Furthermore, Japanese Patent Laid-open Publication, No.61-36595 teaches a vacuum thermal insulator characterized by uniformly-distributed carbon powder in various powdery pulverulent substances. In one of its embodied examples, carbon black is distributed uniformly into silica having 100 nm in particulate diameter, and obtains an improvement of 20% in the thermal insulation property under the optimum condition.

Moreover, Japanese Patent Examined Publication, No.08-20032 discloses a vacuum thermal insulator which uses fine powder produced from fumes generated in the production of ferrosilicon. It also discloses the vacuum thermal insulator in which the fine powder contains at least carbon in an amount of 1 wt % or more. This thermal insulator exhibits an improvement of 23% in the thermal insulation property.

With regard to the pearlite in Patent Publication 60-33479, the silica having particulate diameter of 100 nm in Patent Publication 61-36595, and the fumes generated in the production of ferrosilicon in Patent Publication 8-20032, all containing powdery carbon or other forms of carbon, however, the pearlite, the silica having particulate diameter of 100 nm, and the fumes generated in the production of ferrosilicon, as used for the base material do not exhibit any distinguishable effect as the core member of the vacuum thermal insulator. Therefore, they do not improve the thermal insulation property substantially, and their effects of improvement are only up to about 20% when compared with other vacuum thermal insulators, even though these materials are intended for a large improvement by containing powdery carbon and the other forms of carbon.

In the specification that uses carbon black as the powdery carbon, the carbon black exhales gas over time, since it generally is a sooty product obtained through imperfect combustion of oil content and it contains organic gas as impurity. Thus, it has had a problem that an increase in an internal pressure of the vacuum thermal insulator causes degradation of the thermal insulation property. In addition, reaction-active radicals such as carbonyl group present in the carbon black at ends of their molecular structures react with moisture in air so as to also produce gas over time, thereby increasing the internal pressure of the vacuum thermal insulator and degrading the thermal insulation property in the similar manner.

Porous bodies are generally used as the core member, which can be classified broadly into one of continuous foam, fibrous group, and pulverulent group.

Among them, silica powder is often used as one of the pulverulent group vacuum insulator materials. Vacuum thermal insulator that uses silica powder is superior in the thermal insulation property over a long duration of time, although it falls behind the fibrous group material in the initial thermal insulation property.

However, because being powdery, this material has poor workability, and is hardly formed in an irregular shape since the powder is to be enveloped in an inner enveloping member when being used. Moreover, it also impairs work environment as the powder disperses when being disposed. There have been some attempts for improvement by making silica powder into compact form. However, various kinds of binder need to be used because of difficulties in molding the silica powder itself into porous bodies.

For instance, Japanese Patent Examined Publication, No.04-46348 discloses a vacuum thermal insulator having a formed body made of wet silica mixed and compressed with fiber reinforcement.

This includes a form having radiation inhibitor compressed, if there are large gradients in temperature between the wet silica and the fiber reinforcement and between walls in which the vacuum thermal insulator is used.

Moreover, Japanese Patent Examined Publication, No.05-66341 —discloses a vacuum thermal insulator including a formed body made of dry silica, wet silica and fiber reinforcement, which are mixed, distributed, and compressed.

A formed body is formed in which the dry silica and the wet silica supplement each other by their respective features of low coefficient of thermal conductivity and easiness of press-working, with addition of mixing fiber reinforcement into it.

However, it is not feasible to form the body only with the silica powder.

Even if the wet silica is mixed, stirred, and compression-formed with fibrous material, as taught in Patent Publication, No. 04-46348, the formed body is so brittle that it crumbles easily when being picked up with a hand. In addition, it also raises heavy powdery dust thus deteriorating workability and ease of handling. If it is formed into a cylindrical shape, for example, it crumbles so quickly. Also, since lacking flexibility, the body has a limitation in the field of applications.

Furthermore, even if being formed by mixing and stirring the wet silica, dry silica and the fiber reinforcement, and compression forming them, as taught by Patent Publication, No.05-66341, the body is not easily formed, and is brittle because it contains the wet silica mixed to it. In addition, it raises heavy powdery dust, and lacks flexibility.

DISCLOSURE OF THE INVENTION

A portable information device such as a notebook type computer having a highly efficient thermal insulator blocks a transfer of heat between an internal heating component and a device enclosure without causing impediment to a low-profile design. This information device suppresses temperature rise on a surface of the device, so as not to give uncomfortable feeling to a user. The information device is also provided with an efficient thermal insulator for blocking a transfer of heat between the internal heating component and a built-in mounting case of an external expansion unit, thereby suppressing temperature rise of the external expansion unit and preventing malfunction of the unit.

DESCRIPTION OF THE PREFERRED EMBODIMENTS (First Exemplary Embodiment)

Figure 1:
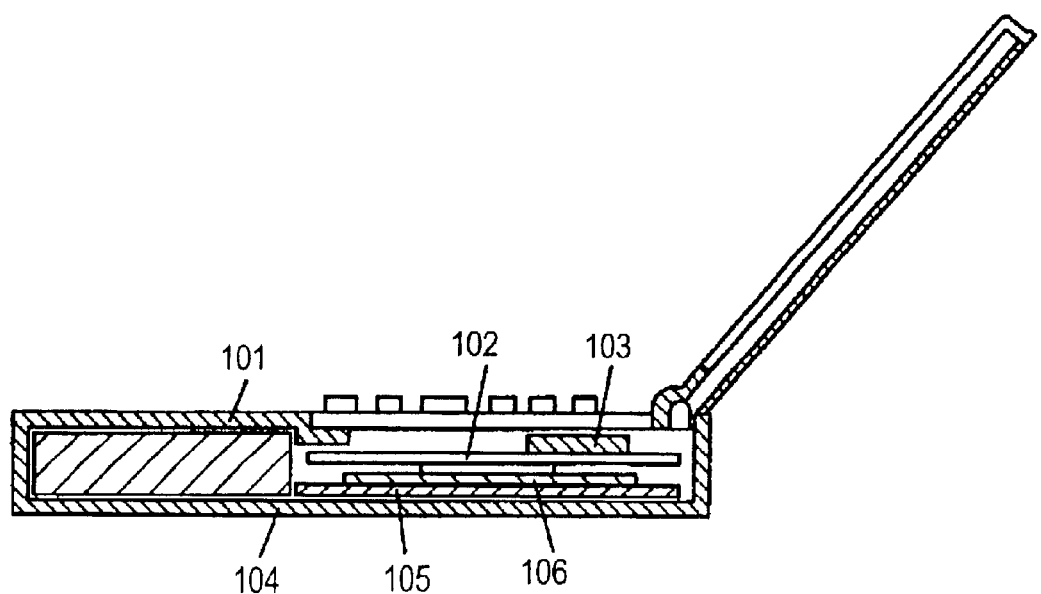
FIG. 1 is a schematic view of a notebook type computer according to a first exemplary embodiment of the present invention.

FIG. 1 shows a notebook type computer 101 according to the first exemplary embodiment. The computer 101 includes a vacuum thermal insulator 105 separating between heating component 103 on an internal main board 102 and a bottom of a device enclosure 104, and a heat sink 106. This computer alleviates temperature rise on a surface of the device, and prevents heat from being transferred to a user, since it can effectively block transfer of the heat to the bottom surface.

(Second Exemplary Embodiment)

Figure 2:
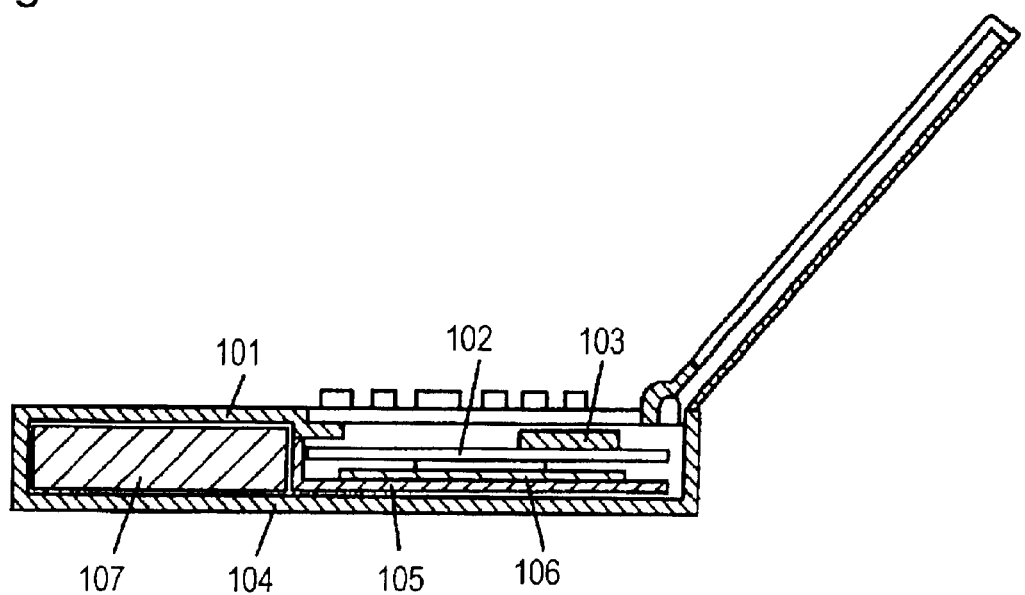
FIG. 2 is a schematic view of a notebook type computer according to a second exemplary embodiment of the invention.

FIG. 2 shows a notebook type computer 101 according to the second exemplary embodiment. The computer 101 includes a vacuum thermal insulator 105 separating between a heating component 103 on an internal main board 102 and a device enclosure 104 at its bottom side, and a heat sink 106. In this embodiment, the vacuum thermal insulator is formed into a shape of letter "L", to isolate a hard disk drive (HDD) from the heating component. This computer suppresses temperature rise on a surface of the device, and prevents heat from being transferred to a user, since it can effectively block transfer of the heat to the bottom surface. It also protects components that are sensitive to heat such as the HDD 107 within the device.

(Third Exemplary Embodiment)

Figure 3:
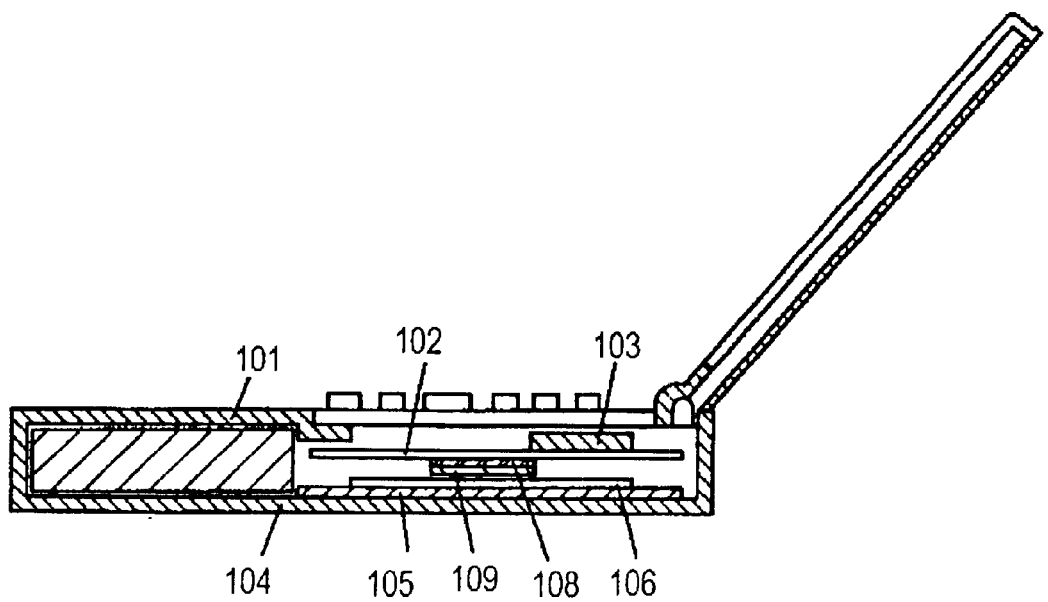
FIG. 3 is a schematic view of a notebook type computer according to a third exemplary embodiment of the invention.

FIG. 3 shows a notebook type computer 101 according to the third exemplary embodiment. The computer 101 includes a vacuum thermal insulator 105 separating between a heating component 103 on an internal main board 102 and a bottom of a device enclosure 104, another vacuum thermal insulator 109 separating between the heating component 103 and an expansion unit mounting case 108, and a heat sink 106. This computer suppresses temperature rise on a surface of the device, and prevents heat from being transferred to a user, since it can effectively block transfer of the heat to the bottom surface. The computer also suppresses temperature rise of the external expansion unit so as to avoid malfunction of the unit, because the computer effectively blocks transfer of the heat to the external expansion unit.

(Fourth Exemplary Embodiment)

Figure 4A:
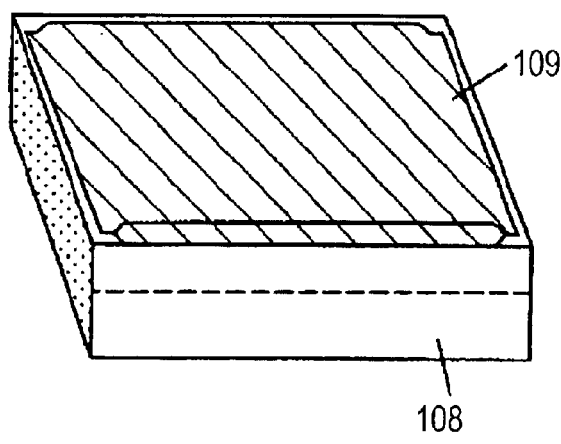
FIG. 4A and FIG. 4B are schematic illustrations of an expansion unit mounting case according to a fourth exemplary embodiment of the invention.
Figure 4B:
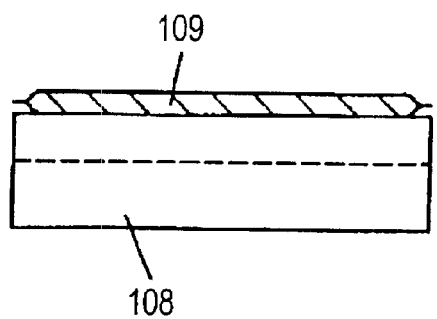

FIG. 4A is a perspective view of an expansion unit mounting case according to the fourth exemplary embodiment, and FIG. 4B is a side view of the same case. The vacuum thermal insulator 109 is attached to the expansion unit mounting case 108.

(Fifth Exemplary Embodiment)

Figure 5:
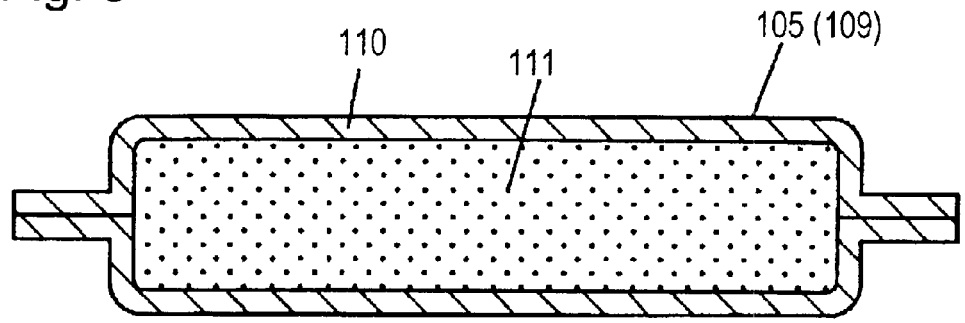
FIG. 5 is a sectional view of a vacuum thermal insulator according to a fifth exemplary embodiment of the invention.

FIG. 5 is a sectional view of each of vacuum thermal insulators 105 and 109 according to the fifth exemplary embodiment. An enveloping member 10 is filled with a core member consisting of inorganic powder 111.

(Sixth Exemplary Embodiment)

Figure 6:
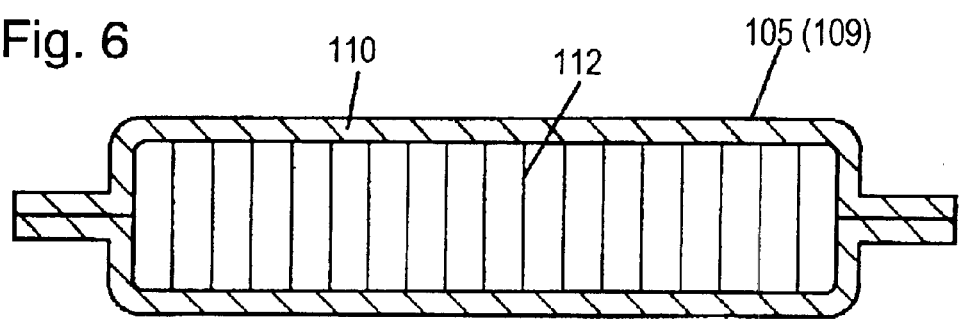
FIG. 6 is a sectional view of a vacuum thermal insulator according to a sixth exemplary embodiment of the invention.

FIG. 6 is a partly sectioned schematic illustration of the vacuum thermal insulator 105 or 109 according to the sixth exemplary embodiment. An enveloping member 110 is filled with a core member consisting of inorganic fiber 112.

(Seventh Exemplary Embodiment)

Figure 7:
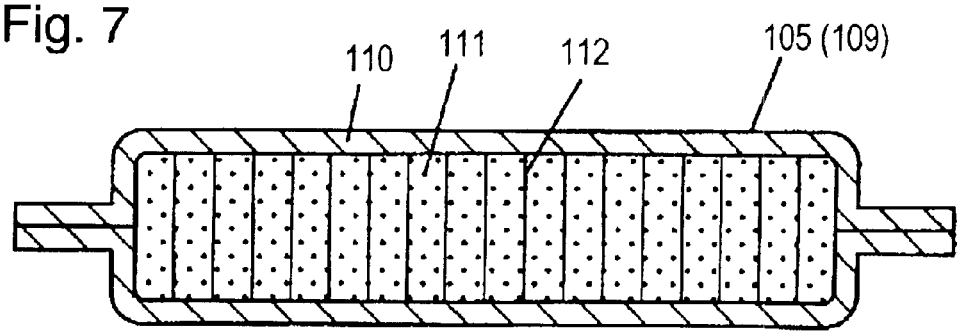
FIG. 7 is a sectional view of a vacuum thermal insulator according to a seventh exemplary embodiment of the invention.

FIG. 7 is a sectional view of one of vacuum thermal insulators 105 and 109 according to the seventh exemplary embodiment. An enveloping member 110 is filled with a core member consisting of inorganic powder 111 and inorganic fiber 112.

(Eighth Exemplary Embodiment)

Figure 8:
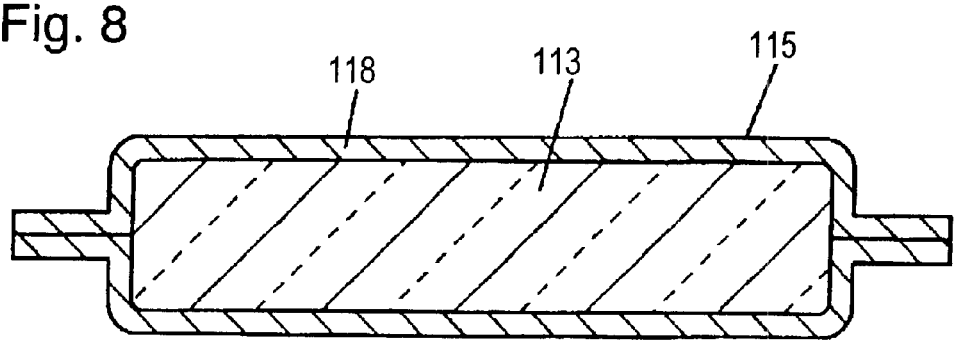
FIG. 8 is a sectional view of a vacuum thermal insulator according to an eighth exemplary embodiment of the invention.

FIG. 8 is a sectional view of one of vacuum thermal insulators 105 and 109 according to the eighth exemplary embodiment. An enveloping member 110 is filled with a core member consisting of an open-cell polyurethane foam 113.

(Ninth Exemplary Embodiment)

Figure 9:
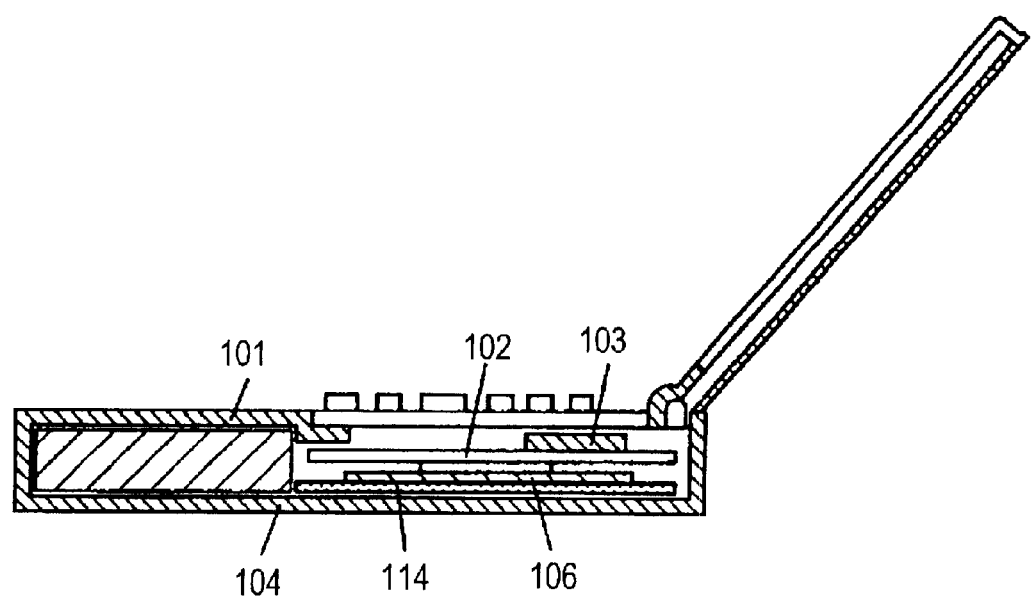
FIG. 9 is a schematic view of a notebook type computer according to a ninth exemplary embodiment of the invention.

FIG. 9 shows a notebook type computer 101 according to the ninth exemplary embodiment. The computer 101 includes a microporous body 114 consisting of dried gel for separating between a heating component 103 on an internal main board 102 and a device enclosure 104, and a heat sink 106.

Each vacuum thermal insulator according to the above-described exemplary embodiments of this invention includes a core member and an enveloping member which is filled with the core member and is sealed under a reduced pressure. Internal pressure of 100 Torr or less is desirable, and 10 Torr or less is more desirable. In addition, adsorbent may be used. In order to reduce a thickness of the notebook type computer, 5 mm or less in thickness of the vacuum thermal insulator is desirable, and 2 mm or less is even more desirable.

The core member of the vacuum thermal insulator may employ a continuously foamed body made of polymeric material such as polystyrene and polyurethane, inorganic and organic powder, inorganic and organic fiber material, and the like. Inorganic powder, inorganic fiber, and mixture of them are especially preferable.

The enveloping member includes a surface protective layer, a gas barrier layer, and a heat welding layer, and each layer consists of a lamination of at least one type of film. The surface protective layer may employ an axially oriented product of polyethylene terephthalate film or polypropylene film and the like are. The gas barrier layer may employ a metallized film, an inorganic substance deposited film, a metal foil, and the like. For the heat welding layer, a low density polyethylene film, a high density polyethylene film, a polypropylene film, a polyacrylonitrile film, a non-oriented polyethylene terephthalate film, and the like are used.

Any of powdery inorganic materials such as agglomerate silica powder, pulverized powder of foamed pearlite, diatomaceous earth powder, calcium silicate powder, calcium carbonate powder, clay, talc, and the like can be used for the inorganic powder. Agglomerate silica powder having a secondary agglomerate diameter of 20 $\mu$m or less is especially desirable.

Fiberized inorganic materials such as glass wool, ceramic fiber, rock wool, and the like can be used for the inorganic fiber. Their form such as nonwoven fabric form, woven form, cottony form is not a matter of importance. In addition, organic binder may be used to aggregate the inorganic fiber.

Microporous bodies exhibiting good heat insulating property, including inorganic oxide aerogel such as silica aerogel, alumina aerogel, and so on, inorganic aerogel such as polyurethane aerogel, polyisocyanate aerogel, phenolic series aerogel, and the like are suitable for the microporous body of dried gel. Alternatively it can be a mixture of two or more kinds of aerogel. Further, any forms such as granular form and monolith form can be useful.

In any of the above-described exemplary embodiments, the thermal insulator for blocking the heat transfer between the internal heating component and the device enclosure, and another thermal insulator for blocking the heat transfer between the heating component and the expansion unit mounting case can be used independently, or they may be used together.

Described hereinafter are actual embodiment samples of the thermal insulators. However, the thermal insulators of the invention are not restricted to only those taught herein.

(Embodiment Sample 1.1)

An open-cell polyurethane foam was used for a core member of a vacuum thermal insulator. An enveloping member consisting of a surface protective layer of polyethylene terephthalate film, a gas barrier layer of aluminum foil and a heat welding layer of non-oriented polypropylene was used. The enveloping member was filled with the open-cell polyurethane foam, and it was sealed under a pressure of 0.1 Torr, to prepare the vacuum thermal insulator. A thickness of the vacuum thermal insulator is 1.5 mm. The vacuum thermal insulator was placed in the notebook type computer, as shown in FIG. 1. A temperature measured on a bottom surface was 46° C., and an effectiveness of the insulation was verified since it was lower than a blank sample by 4° C.

(Embodiment Sample 1.2)

Agglomerate silica powder was used for a core member of a vacuum thermal insulator. The same enveloping member as that described in the embodiment sample 1.1 was used.

The enveloping member was filled with the agglomerate silica powder, and it was sealed under a pressure of 0.1 Torr, to prepare the vacuum thermal insulator. A thickness of the vacuum thermal insulator is 1.5 mm. The vacuum thermal insulator was placed in the notebook type computer, as shown in FIG. 1. A temperature measured on a bottom surface was 46° C., when measured, and an effectiveness of the insulation was verified since it was lower than a blank sample by 4° C. In addition, it was easier to place the thermal insulator than in the case of the embodiment sample 1.1, because the insulator has flexibility.

(Embodiment Sample 1.3)

Inorganic fiber consisting of silica-alumina was used for a core member of vacuum thermal insulator. The same enveloping member as that described in the embodiment sample 1.1 was used. The enveloping member was filled with the inorganic fiber, and was sealed under a pressure of 0.1 Torr, to prepare the vacuum thermal insulator. A thickness of the vacuum thermal insulator is 1.5 mm. The vacuum thermal insulator was placed in the notebook type computer, as shown in FIG. 1. A temperature measured on a bottom surface was lower than a blank sample by 5° C., and an effectiveness of the insulation was verified. In addition, since the fibrous material raises no powdery dust, the insulator can be handled more easily than in the case of the embodiment sample 1.2. The insulator can be filled-in than that of the embodiment sample 1.1, since being flexible.

(Embodiment Sample 1.4)

A material used for a core member of a vacuum thermal insulator was prepared by preliminarily mixing agglomerate silica powder and inorganic fiber consisting of silica-alumina, and forming it in shape. The same enveloping member as that described in the embodiment sample 1.1 was used. The enveloping member was filled with the core member, and was sealed under a pressure of 0.1 Torr, to prepare the vacuum thermal insulator. A thickness of the vacuum thermal insulator is 1.5 mm. The vacuum thermal insulator was placed in the notebook type computer, as shown in FIG. 1. A temperature measured on a bottom surface was lower than a blank sample by 5.5° C., and an effectiveness of the insulation was thus verified. In addition, since powder and fiber are mixed, their void dimensions became smaller than those of the embodiment samples 1.2 and 1.3, and thus the insulating property was improved. Also, the insulator is handled more easily than in the case of the embodiment sample 1.2, since it did not raise powdery dust. Furthermore, the insulator is filled-in more easily than that of the embodiment sample 1.1, since being flexible.

(Embodiment Sample 1.5)

A monolith body of silica aerogel in a thickness of 2 mm was used for a microporous body of dried gel. This silica aerogel was placed in the notebook type computer, as shown in FIG. 6. A temperature measured a bottom surface was lower than a blank sample by 4° C., and thus an effectiveness of the insulation was verified. The silica aerogel, since providing the effectiveness of insulation without requiring vacuum-evacuation, put a less burden on manufacturing as compared to the vacuum thermal insulator.

(Comparative Sample 1.1)

A temperature on a bottom surface of a notebook type computer not provided with a thermal insulator was 50° C.

(Comparative Sample 1.2)

Polyurethane foam having 1.5 mm thickness was used as a thermal insulator, and was placed in a notebook type computer in the same manner as the embodiment sample 1.5. Although a temperature on a bottom surface decreased by 1° C., the effectiveness of insulation was small.

(Tenth Exemplary Embodiment)

Figure 10:
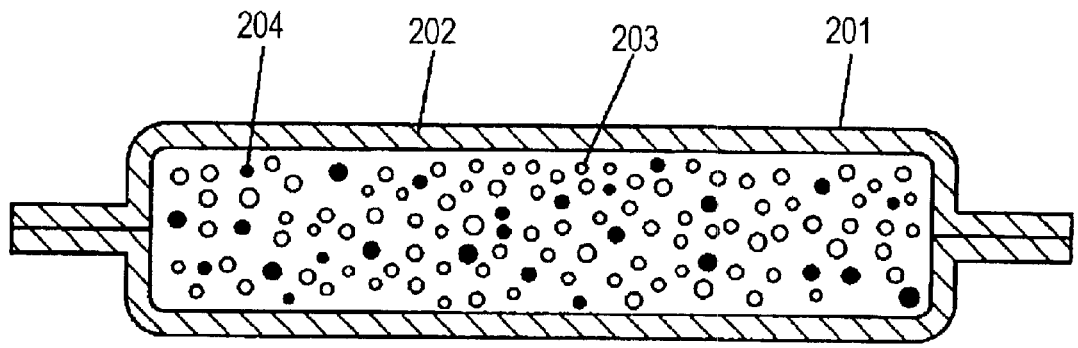
FIG. 10 is a sectional view of a vacuum thermal insulator according to a tenth exemplary embodiment of the invention.

FIG. 10 is a sectional view of vacuum thermal insulator 201 according to the tenth exemplary embodiment, in which enveloping member 202 having a metallic foil layer and a thermoplastic polymer layer is filled with uniformly mixed fumed silica 203 and powdery carbon material 204.

In a vacuum thermal insulator, the core member is filled and sealed in the enveloping member under a reduced pressure. In addition, such materials as moisture adsorbent and gas absorbent may be used, including physical adsorbents such as synthetic zeolite, activated charcoal, active alumina, silica gel, dawsonite, hydrotalcite, and the like, as well as chemical absorbents such as oxides of alkali metal and alkaline earth metal, hydroxides, and the like. Alternatively, the core member may be put into the enveloping member and sealed after being enclosed in a non-woven fabric. Or, the core member may be dried before being vacuum-sealed.

Oxidized silicon compound having a variety of particulate diameters manufactured by dry processing, such as silicic acid and the like made by the arc method, and silicic acid and the like made by pyrolysis may be used as the fumed silica. Mixture of fumed silica having a variety of particulate diameters can also be used. For instance, any products that are made irregularly during a period of change-over in mass production between A-product and B-product of respectively controlled particulate diameters may be used, even though particulate diameters of such products vary between those of A-product and B-product, since they are not controlled due to the change-over. In this case, the vacuum thermal insulators can be made at a lower cost. However, it is desirable to use those having an average primary particulate diameter of 50 nm or less, if greater importance is attached to the thermal insulation property. Or, it is even more desirable to use those of 10 nm or less if a better property is needed.

Any carbon materials such as carbon black, graphitized carbon powder, activated charcoal, acetylene black, and the like can be used as the powdery carbon material, so long as they are pulverized. Carbon black is readily useful because it is widely available at reasonably low price. When carbon black is used, however, it is preferable to use those having a specific surface area of less than 100 $m^2/g$, in order to control time-dependent exhalation of gases and to maintain the excellent thermal insulation property for a long period of time. It is also preferable to use graphitized carbon powder for the same reasons.

For the enveloping member, any material is usable if it is capable of sealing off the core member from the external air. Thin sheet metals such as stainless steel, aluminum, iron, and the like, or a laminated material of sheet metal and plastic film, and so on may be used. The laminated material may desirably be constructed with a surface protective layer, a gas barrier layer, and a heat welding layer. An axially oriented product of polyethylene terephthalate film or polypropylene film and the like are usable for the surface protective layer. A nylon film and the like, upon being provided on an exterior surface, can increase flexibility, so as to improve a resistance to bending. A film of metallic foil such as aluminum and metallized film is usable for the gas barrier layer. It is desirable to use the metallized film, however, in order to reduce a leakage of heat and to obtain good insulating effectiveness. It is preferable to use such materials as polyethylene terephthalate film, ethylene vinyl-alcohol copolymer film, polyethylene naphthalate film, and the like covered with vaporized metal deposit. For the heat welding layer, a low-density polyethylene film, high-density polyethylene film, polypropylene film, polyacrylonitrile film, non-oriented polyethylene terephthalate film, and the like are usable.

(Eleventh Exemplary Embodiment)

Figure 11:
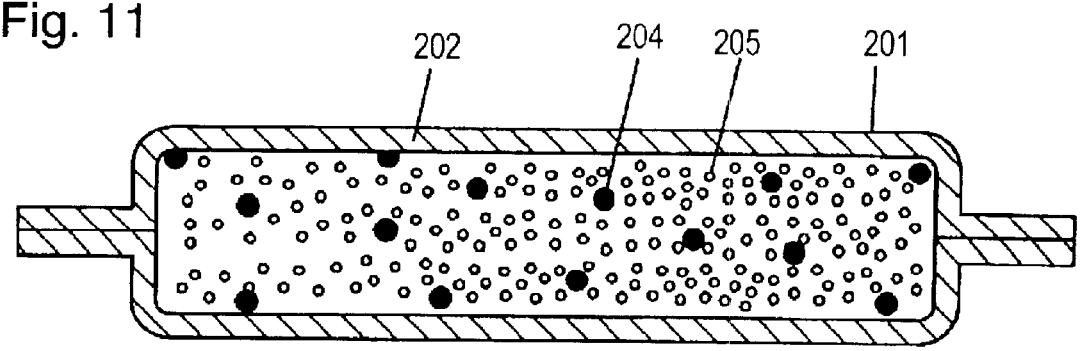
FIG. 11 is a sectional view of a vacuum thermal insulator according to an eleventh exemplary embodiment of the invention.

FIG. 11 is a sectional view of vacuum thermal insulator 201 according to the eleventh exemplary embodiment, in which enveloping member 202 having a metallic foil layer and a thermoplastic polymer layer is filled with uniformly mixed fumed silica 205 of 50 nm or less in average primary particulate diameter and powdery carbon material 204.

(Twelfth Exemplary Embodiment)

Figure 12:
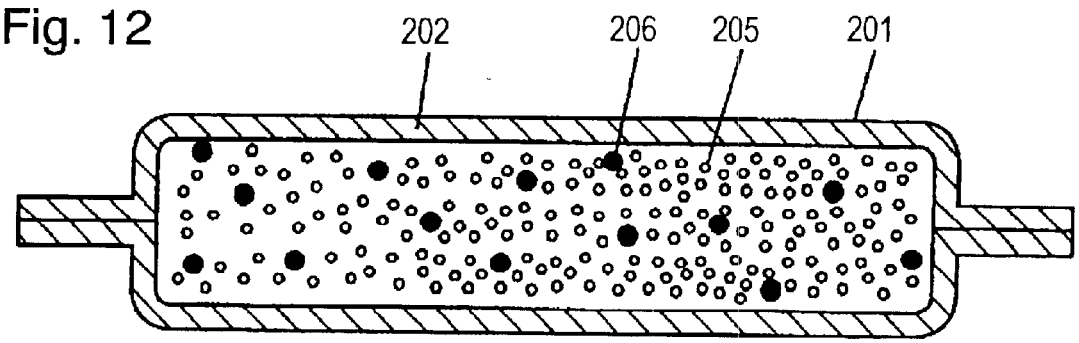
FIG. 12 is a sectional view of a vacuum thermal insulator according to a twelfth exemplary embodiment of the invention.

FIG. 12 is a sectional view of vacuum thermal insulator 201 according to the twelfth exemplary embodiment, in which enveloping member 202 having a metallized film layer and a thermoplastic polymer layer is filled with uniformly mixed fumed silica 205 of 50 nm or less in average primary particulate diameter and carbon black 206 having a specific surface area of less than 100 $m^2/g$.

(Thirteenth Exemplary Embodiment)

Figure 13:
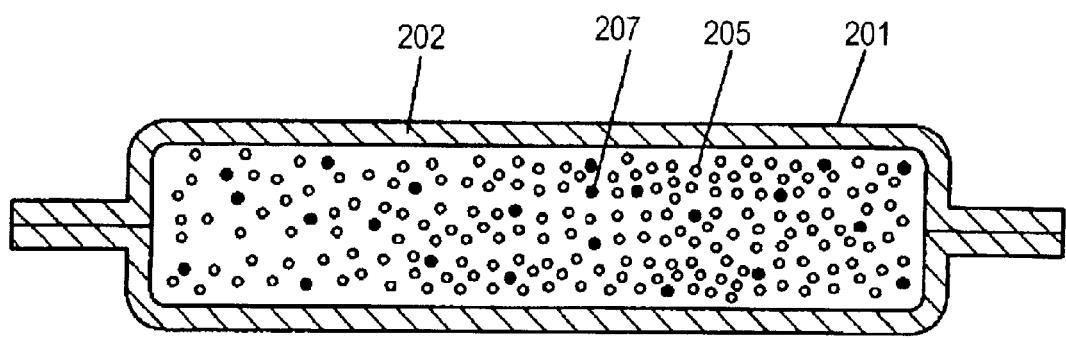
FIG. 13 is a sectional view of a vacuum thermal insulator according to a thirteenth exemplary embodiment of the invention.

FIG. 13 is a sectional view of vacuum thermal insulator 201 according to the thirteenth exemplary embodiment, in which enveloping member 202 having a metallized film layer and a thermoplastic polymer layer is filled with uniformly mixed fumed silica 205 of 50 nm or less in average primary particulate diameter and graphitized carbon powder 207.

(Fourteenth Exemplary Embodiment)

Figure 14:
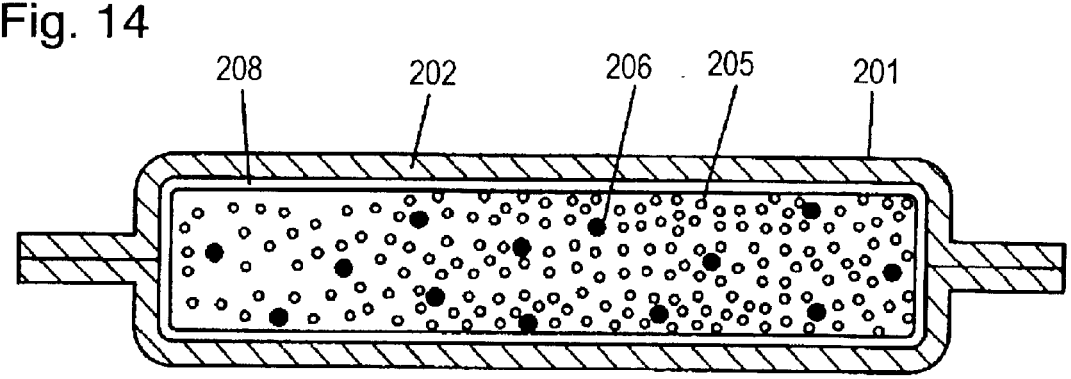
FIG. 14 is a sectional view of a vacuum thermal insulator according to a fourteenth exemplary embodiment of the invention.

FIG. 14 is a sectional view of vacuum thermal insulator 201 according to the fourteenth exemplary embodiment, in which enveloping member 202 having a metallized film layer and a thermoplastic polymer layer is filled with uniformly mixed fumed silica 205 of 50 nm or less in average primary particulate diameter and carbon black 206 having a specific surface area of less than 100 $m^2/g$, which are prepackaged in nonwoven fabric 208.

(Fifteenth Exemplary Embodiment)

Figure 15:
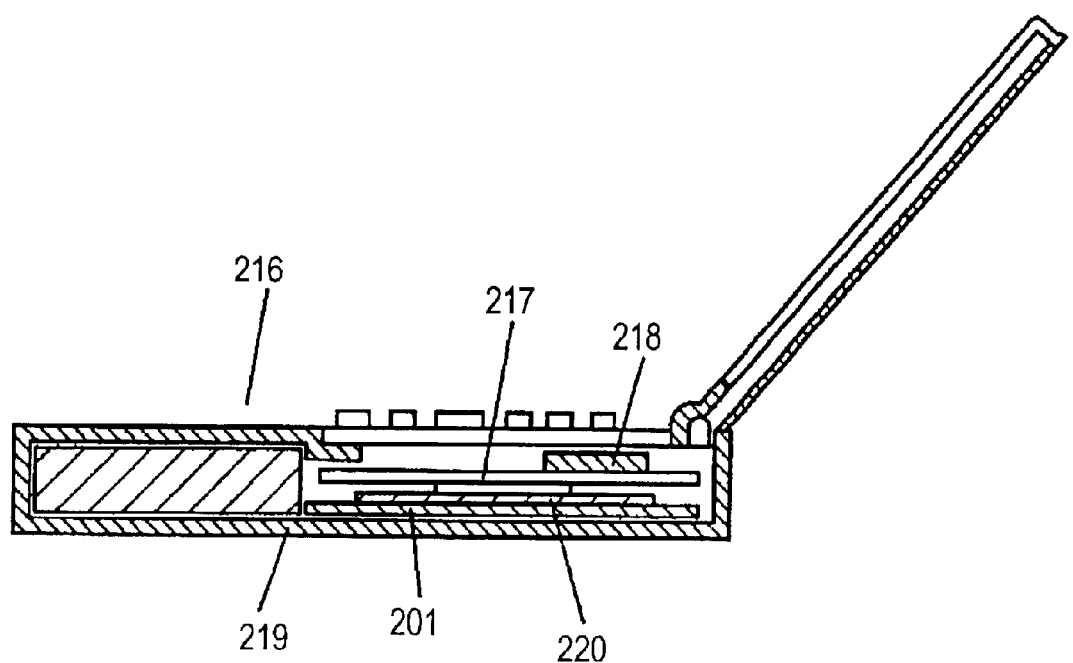
FIG. 15 is a sectional view of a notebook type computer according to a fifteenth exemplary embodiment of the invention.

FIG. 15 is a sectional view of notebook type computer 216 according to the fifteenth exemplary embodiment. Provided therein are vacuum thermal insulator 201 described in the fourteenth exemplary embodiment and heat sink 220, which shield between heating component 218 on main board 217 in the device and a bottom of device enclosure 219. The thermal insulator 201 contains fumed silica of excellent thermal insulation property as a base material, and powdery carbon is uniformly distributed in the base material, thereby providing even better thermal insulation property than the insulator in which only the fumed silica is used as the core member. Also, the enveloping member, since having a metallized film layer reduces leakage of heat, effectively blocks the heat transferred to the bottom surface. It thus reduces temperature rise on the surface of the device, and prevents the heat from being transferred to a user. In addition, the powdery carbon appropriate for the purpose obviates deterioration of the thermal insulation property over duration of time due to an increase in the internal pressure.

The notebook type computer is described as an example, which represents a device that requires the insulation in an operating temperature ranging from the normal temperature to approx. 80° C., and therefore it is by no means restrictive. The present exemplary embodiment is also applicable to, for instance, a thermal insulation of a liquid crystal component from a heating component associated with a CPU in a vehicle navigation system equipped with a liquid crystal display panel.

(Sixteenth Exemplary Embodiment)

Figure 16:
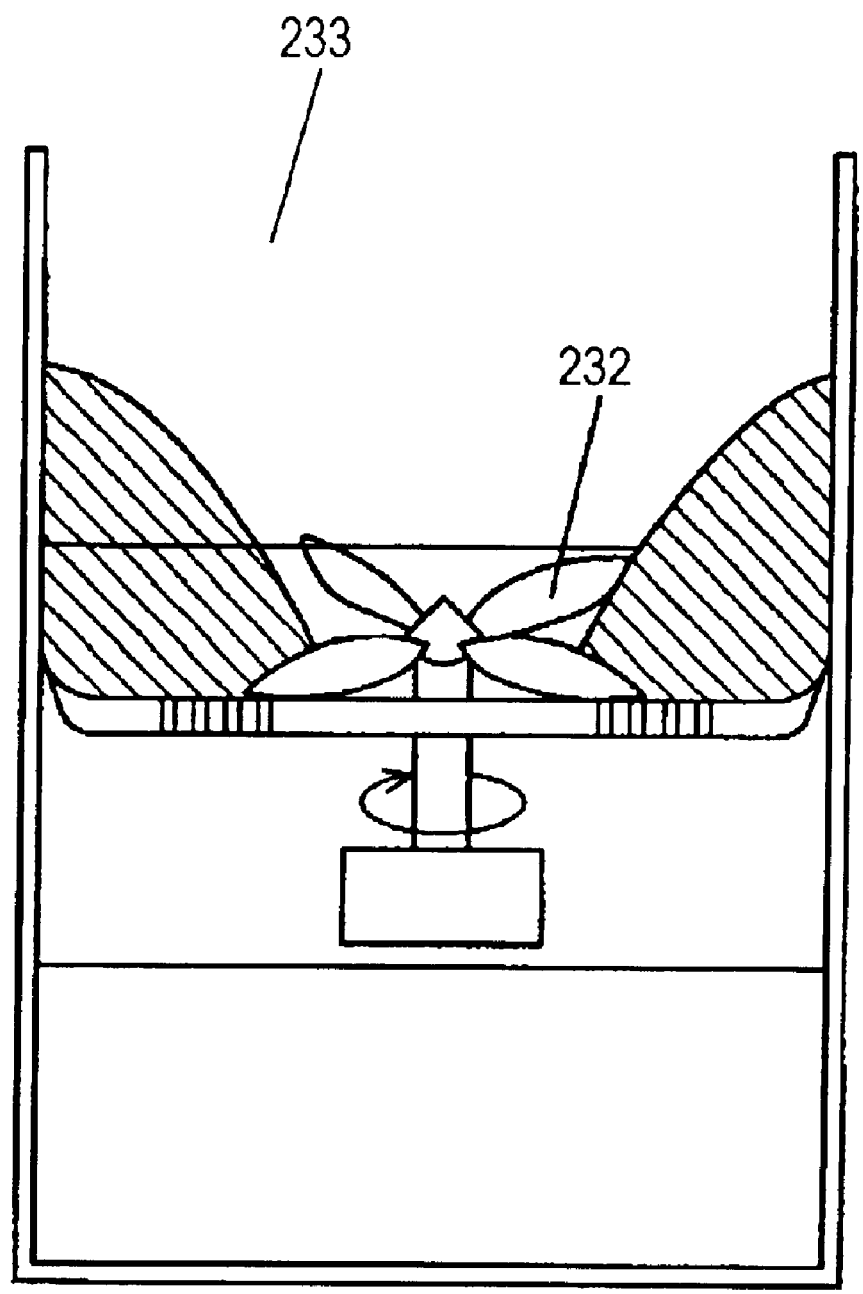
FIG. 16 illustrates a mixing container according to a sixteenth exemplary embodiment of the invention.

FIG. 16 shows mixing container 233 having stirring blades 232 used in the method of manufacturing a vacuum thermal insulator according to the sixteenth exemplary embodiment. The stirring blades provided for uniform distribution of powdery particles grind secondary and tertiary agglomerates of fumed silica contained in raw material. Since this makes the fumed silica suitable for being distributed uniformly in the powdery carbon material, it can avoid deterioration of the thermal insulation property due to poor distribution developed partially.

(Seventeenth Exemplary Embodiment)

Figure 17:
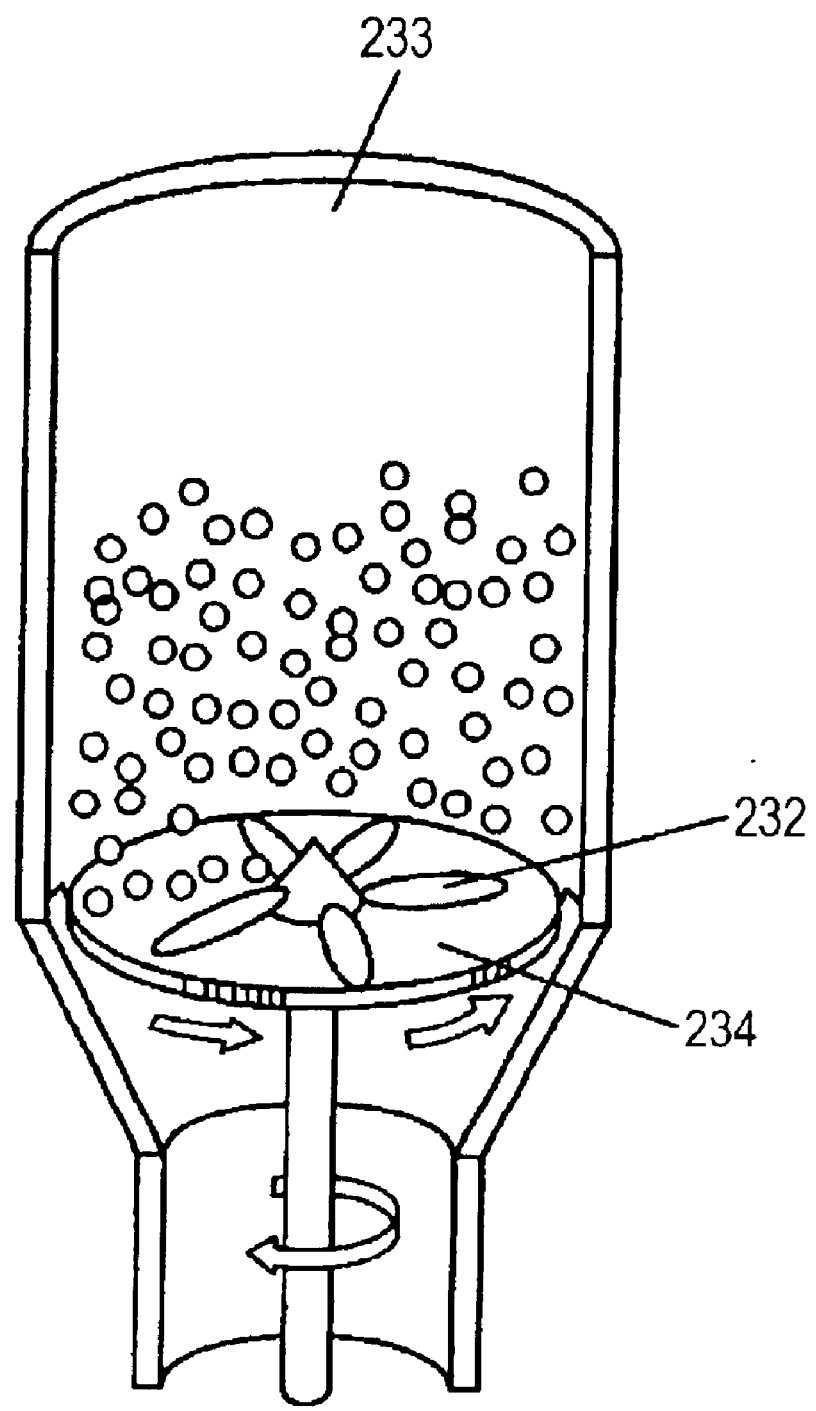
FIG. 17 illustrates another mixing container according to a seventeenth exemplary embodiment of the invention.

FIG. 17 shows mixing container 233 having stirring blades 232 used in the method of manufacturing a vacuum thermal insulator according to the seventeenth exemplary embodiment. The container 233 is so constructed that either the mixing container itself or rotor 234 in a bottom also rotates in addition to the rotation of the stirring blades 232. The powder is thus rotatory mixed. This reduces a time required for grinding secondary and tertiary agglomerates of the fumed silica contained in raw material, as compared to the mixing container used in the sixteenth exemplary embodiment, thereby performing more efficient process of uniform distribution.

In this method of manufacturing the vacuum thermal insulator, any mixing container is usable if having a stirring blade that is capable of grinding the secondary and tertiary agglomerates of the fumed silica contained in the raw material. A shape of the mixing container, whether it is cylindrical, spherical or cubical, is not a matter of importance.

Certain embodiment samples according to the foregoing exemplary embodiments will be described hereinafter. However, the present invention is not restrictive only to those described hereinbelow.

(Embodiment Sample 2.1)

Core member used here consists of 89 wt % fumed silica of a variety of average primary particulate diameters, 10 wt % carbon black having a specific surface area of 50 $m^2/g$ as the powdery carbon material, and 1% of other material, which are uniformly mixed in the mixing container equipped with stirring blades. The core member is packed into enveloping members made of nonwoven fabric of polyester. They are then packed in enveloping members of laminate enveloping member, each of which consists of a surface protective layer of polyethylene terephthalate film, a gas barrier layer of ethylene vinyl-alcohol copolymer film with metallized aluminum, and a heat welding layer of non-oriented polypropylene. And they are sealed under a pressure of 133 Pa with a thermal welding machine, to obtain vacuum thermal insulators.

Table 201 shows a resultant measurement of a coefficient of thermal conductivity for each of the vacuum thermal insulators.

As obvious from Table 201, adding the carbon black into the fumed silica of a variety of average primary particulate diameters can improve the coefficient of thermal conductivity between 30% and 47%, as compared with the fumed silica containing no additives. Also, the improvements are more effective, since they reach 40% or greater especially when the average primary particulate diameter of the fumed silica is 50 nm or smaller.

TABLE 201

| Fumed silica Content (wt %) | 89 | 89 | 89 | 89 | 89 | 89 | 89 |
|---|---|---|---|---|---|---|---|
| Carbon black Content (wt %) | 10 | 10 | 10 | 10 | 10 | 10 | 10 |
| Other material Content (wt %) | 1 | 1 | 1 | 1 | 1 | 1 | 1 |
| Fumed silica, average primary particle dia. (nm) | 7 | 16 | 30 | 50 | 80 | 100 | 200 |
| Carbon black, specific surface area (m$^2$/g) | 50 | 50 | 50 | 50 | 50 | 50 | 50 |
| Initial coefficient of thermal conductivity (kcal/mh °C.) | 0.0027 | 0.0033 | 0.0034 | 0.0034 | 0.0044 | 0.0044 | 0.0047 |
| Coefficient of thermal conductivity, ratio of Reduction to blank (%) | 47 | 40 | 40 | 40 | 30 | 30 | 30 |
| Fumed silica Content (wt %) | 100 | 100 | 100 | 100 | 100 | 100 | 100 |
| Carbon black Content (wt %) | 0 | 0 | 0 | 0 | 0 | 0 | 0 |
| Other material Content (wt %) | 0 | 0 | 0 | 0 | 0 | 0 | 0 |
| Fumed silica, average primary particle dia. (nm) | 7 | 16 | 30 | 50 | 80 | 100 | 200 |
| Carbon black, specific Surface area (m$^2$/g) | 50 | 50 | 50 | 50 | 50 | 50 | 50 |
| Initial coefficient of thermal conductivity (kcal/mh °C.) | 0.0051 | 0.0055 | 0.0057 | 0.0057 | 0.0062 | 0.0062 | 0.0067 |

(Embodiment Sample 2.2)

Core member used here consists of 89 wt % fumed silica having an average primary particulate diameter of 7 nm, 10 wt % carbon black having a variety of specific surface areas as the powdery carbon material, and 1% of other material, which are uniformly mixed in a mixing container equipped with stirring blades. The core member is packed into enveloping members made of nonwoven fabric of polyester. They are then packed in enveloping members of laminate enveloping member, each of which consists of a surface protective layer of polyethylene terephthalate film, a gas barrier layer of ethylene vinyl-alcohol copolymer film with metallized aluminum, and a heat welding layer of non-oriented polypropylene, and they are sealed under a pressure of 133 Pa with a thermal welding machine, to obtain vacuum thermal insulators.

Table 202 shows resultant measurement of a coefficient of thermal conductivity for each of the vacuum thermal insulators.

As observable in Table 202, adding the 10 wt % carbon black of a variety of specific surface areas into the fumed silica can improve the coefficient of thermal conductivity between 43% and 51%, as compared with the fumed silica containing no additives.

Also, the larger the specific surface area of the carbon black, the greater the effectiveness of improvement in the coefficient of thermal conductivity. However, the coefficients of thermal conductivity become low after the elapse of ten days, when carbon black having a specific surface area of 100 m$^2$/g or larger is added. This is caused by an increase in the internal pressure due to gases exhaled by the carbon black.

Since the amount of added carbon black is 10%, it does not substantially reduce the coefficient of thermal conductivity even if the carbon black has the specific surface area of 100 m$^2$/g or larger

TABLE 202

| Fumed silica content (wt %) | 89 | 89 | 89 | 89 | 89 |
|---|---|---|---|---|---|
| Carbon black content (wt %) | 10 | 10 | 10 | 10 | 10 |
| Other material content (wt %) | 1 | 1 | 1 | 1 | 1 |
| Fumed silica average primary particulate diameter (nm) | 7 | 7 | 7 | 7 | 7 |
| Carbon black specific surface area (m$^2$/g) | 30 | 50 | 80 | 135 | 290 |
| Initial coefficient of thermal conductivity (kcal/mh °C.) | 0.0029 | 0.0027 | 0.0027 | 0.0026 | 0.0025 |
| Coefficient of thermal conductivity, ratio of reduction to blank sample (%) | 40 | 40 | 30 | 30 | 30 |
| Coefficient of thermal conductivity after tenth day (kcal/mh °C.) | 0.0029 | 0.0027 | 0.0027 | 0.0028 | 0.003 |
| Coefficient of thermal conductivity, ratio of reduction to blank sample (%) | 43 | 47 | 47 | 45 | 41 |

(Embodiment Sample 2.3)

Core member used here consists of 59 wt % fumed silica having an average primary particulate diameter of 7 nm, 40 wt % carbon black having a variety of specific surface areas as the powdery carbon material, and 1% of other material, which are uniformly mixed in a mixing container equipped with stirring blades. The core member is packed into enveloping members made of nonwoven fabric of polyester. They are then packed in enveloping members of laminate enveloping member, each of which consists of a surface protective layer of polyethylene terephthalate film, a gas barrier layer of ethylene vinyl-alcohol copolymer film with metallized aluminum, and a heat welding layer of non-oriented polypropylene. Then they are sealed under a pressure of 133 Pa with a thermal welding machine, to obtain vacuum thermal insulators.

Table 203 nshows resultant measurement of a coefficient of thermal conductivity for each of the vacuum thermal insulators.

As observable in Table 203, adding the 40 wt % carbon black of a variety of specific surface areas into the fumed silica can improve the coefficient of thermal conductivity between 37% and 43%, as compared with the fumed silica containing no additives.

However, the coefficients of thermal conductivity become low after the elapse of ten days, when carbon black having a specific surface area of 100 $m^2/g$ or larger is added. This is attributed to an increase in the internal pressure due to gases exhaled by the carbon black, since added amount of the carbon black is 40 wt %, wherein the increase in pressure exerts influence on the coefficients of thermal conductivity more conspicuously than when 10 wt % carbon black is added.

TABLE 203

| | | | | | |
|---|---|---|---|---|---|
| Fumed silica content (wt %) | 59 | 59 | 59 | 59 | 59 |
| Carbon black content (wt %) | 40 | 40 | 40 | 40 | 40 |
| Other material content (wt %) | 1 | 1 | 1 | 1 | 1 |
| Fumed silica average primary particulate diameter (nm) | 7 | 7 | 7 | 7 | 7 |
| Carbon black specific surface area ($m^2/g$) | 30 | 50 | 80 | 135 | 290 |
| Initial coefficient of thermal conductivity (kcal/mh ° C.) | 0.0032 | 0.003 | 0.0031 | 0.003 | 0.0029 |
| Coefficient of thermal conductivity, ratio of reduction to blank sample (%) | 37 | 41 | 39 | 41 | 43 |
| Coefficient of thermal conductivity after tenth day (kcal/mh ° C.) | 0.0032 | 0.003 | 0.0032 | 0.0037 | 0.0038 |
| Coefficient of thermal conductivity, ratio of reduction to blank sample (%) | 37 | 41 | 37 | 27 | 25 |

(Embodiment Sample 2.4)

Core member used here consists of 59 wt % fumed silica having an average primary particulate diameter of 7 nm, 40 wt % graphitized carbon powder having two different specific surface areas, as the powdery carbon material, and 1% of other material, which are uniformly mixed in a mixing container equipped with stirring blades. The core member is packed into enveloping members made of nonwoven fabric of polyester. They are then packed in enveloping members of laminate enveloping member, each of which consists of a surface protective layer of polyethylene terephthalate film, a gas barrier layer of ethylene vinyl-alcohol copolymer film with metallized aluminum, and a heat welding layer of non-oriented polypropylene. Then they are sealed under a pressure of 133 Pa with a thermal welding machine, to obtain vacuum thermal insulators.

Table 204 shows resultant measurement of a coefficient of thermal conductivity for each of the vacuum thermal insulators.

As obvious from Table 204, adding the 40 wt % graphitized carbon powder of two different specific surface areas into the fumed silica improves the coefficient of thermal conductivity between 39% and 41%, as compared with the fumed silica containing no additives.

Furthermore, the graphitized carbon powder having a larger specific surface area gives greater effect to the improvement in coefficient of thermal conductivity.

Moreover, the coefficients of thermal conductivity remain unchanged even after the elapse of ten days in this instance of the graphitized carbon powder. The reason for this is because there is no change in the internal pressure due to gases exhaled over time from the graphitized carbon powder.

TABLE 204

| | | |
|---|---|---|
| Fumed silica content (wt %) | 59 | 59 |
| Graphitized carbon powder content (wt %) | 40 | 40 |
| Other material content (wt %) | 1 | 1 |
| Fumed silica average primary particulate diameter (nm) | 7 | 7 |
| Graphitized carbon powder specific surface area ($m^2/g$) | 50 | 135 |
| Initial coefficient of thermal conductivity (kcal/mh ° C.) | 0.0031 | 0.003 |
| Coefficient of thermal conductivity, ratio of reduction to blank sample (%) | 39 | 41 |
| Coefficient of thermal conductivity after tenth day (kcal/mh ° C.) | 0.0031 | 0.003 |
| Coefficient of thermal conductivity, ratio of reduction to blank sample (%) | 39 | 41 |

(Embodiment Sample 2.5)

Core member used here consists of 89 wt % fumed silica having an average primary particulate diameter of 7 nm, 10 wt % carbon black having a specific surface area of 50 $m^2/g$, as the powdery carbon material, and 1% of other material, which are uniformly mixed in a mixing container equipped with stirring blades. The core member is packed into an enveloping member made of nonwoven fabric of polyester and then packed in an enveloping member of laminate enveloping member, which consists of a surface protective layer of polyethylene terephthalate film, a gas barrier layer of aluminum foil, and a heat welding layer of non-oriented polypropylene. Then the enveloping member is sealed under a pressure of 133 Pa with a thermal welding machine, to obtain a vacuum thermal insulator. A result of measurement with a heat flow meter of a practical coefficient of thermal conductivity of this vacuum thermal insulator, taking into account a leakage of heat, is 0.0033 kcal/mh° C.

(Embodiment Sample 2.6)

Fumed silica and powdery carbon material serving as core member, their mixing ratio and a method of mixing them in this embodiment are the same as that described in the embodiment sample 2.5. The core member is packed into an enveloping member made of nonwoven fabric of polyester. It is then packed in an enveloping member of laminate enveloping member, which consists of a surface protective layer of polyethylene terephthalate film, a gas barrier layer of ethylene vinyl-alcohol copolymer film with metallized aluminum, and a heat welding layer of non-oriented polypropylene. Then it is sealed under a pressure of 133 Pa with a thermal welding machine, to obtain a vacuum thermal insulator.

A result of measurement with a heat flow meter of a practical coefficient of thermal conductivity of this vacuum thermal insulator, taking into account a leakage of heat, is 0.0028 kcal/mh° C., which shows an improvement in the coefficient of thermal conductivity over the embodiment sample 2.5 in which aluminum foil is specified for the gas barrier layer. The reason for this is that the leakage of heat is suppressed by the gas barrier layer of the enveloping member, which is provided with the metallized aluminum on the ethylene vinyl-alcohol copolymer film.

(Embodiment Sample 2.7)

Core member used here consists of 89 wt % fumed silica having an average primary particulate diameter of 7 nm, 10 wt % carbon black having a specific surface area of 50 m$^2$/g, as the powdery carbon material, and 1% of other material, which are uniformly mixed in a mixing container equipped with stirring blades and a rotor rotated in a bottom portion of it. The core member is packed into an enveloping member made of nonwoven fabric of polyester. It is then packed in an enveloping member of laminate enveloping member, which consists of a surface protective layer of polyethylene terephthalate film, a; gas barrier layer of ethylene vinyl-alcohol copolymer film with metallized aluminum, and a heat welding layer of non-oriented polypropylene. Then they are sealed under a pressure of 133 Pa with a thermal welding machine, to obtain a vacuum thermal insulator.

A result of measurement with a heat flow meter of a practical coefficient of thermal conductivity of this vacuum thermal insulator, taking into account a leakage of heat, is 0.0028 kcal/mh° C., showing similar result to the embodiment sample 2.6.

However, a mixture time can be shortened by 20% as compared with the embodiment sample 2.6, since the mixing container equipped with stirring blades mixes the core member by rotating together the rotor in the bottom portion.

(Embodiment Sample 2.8)

A vacuum thermal insulator containing fumed silica with average primary particulate diameter of 7 nm, as described in the embodiment sample 2.1 is placed in a notebook type computer as shown in FIG. 15. A temperature on a bottom surface of the computer is decreased by 5° C. over the one not provided with the thermal insulator. Furthermore, in an accelerated test to evaluate deterioration of the thermal insulator, there is no verifiable deterioration in the thermal insulation property under the condition of a ten-year duration.

(Comparative Sample 2.1)

Core member used for a vacuum thermal insulator here consists of 90 wt % pearlite powder having an average particulate diameter of 8 μm, and 10 wt % carbon black having a specific surface area of 50 m$^2$/g, as the powdery carbon material, which are uniformly mixed in a mixing container equipped with stirring blades. The core member is packed into an enveloping member made of nonwoven fabric of polyester. It is then packed in an enveloping member of laminate enveloping member, which consists of a surface protective layer of polyethylene terephthalate film, a gas barrier layer of aluminum foil, and a heat welding layer of non-oriented polypropylene. Then they are sealed under a pressure of 133 Pa with a thermal welding machine, to obtain the vacuum thermal insulator.

A coefficient of thermal conductivity of this vacuum thermal insulator is 0.0052 kcal/mh° C.

A coefficient of thermal conductivity of another vacuum thermal insulator containing the pearlite powder only is 0.0065 kcal/mh° C. Therefore, adding the 10 wt % carbon black to the pearlite powder reduces only 20%, which is smaller in effect of improvement of the thermal insulation property as compared to those of the present exemplary embodiments.

(Comparative Sample 2.2)

Core member used for a vacuum thermal insulator here consists of 90 wt % pearlite powder having an average particulate diameter of 241 μm, and 10 wt % carbon black having a specific surface area of 50 m$^2$/g, as the powdery carbon material, which are uniformly mixed in a mixing container equipped with stirring blades. The core member is packed into an enveloping member made of nonwoven fabric of polyester. It is then packed in an enveloping 3C member of laminate enveloping member, which consists of a surface protective layer of polyethylene terephthalate film, a gas barrier layer of aluminum foil, and a heat welding layer of non-oriented polypropylene. Then they are sealed under a pressure of 133 Pa with a thermal welding machine, to obtain the vacuum thermal insulator.

A coefficient of thermal conductivity of this vacuum thermal insulator is 0.0050 kcal/mh° C.

A coefficient of thermal conductivity of another vacuum thermal insulator containing the pearlite powder only is 0.0058 kcal/mh° C. Thus, adding the 10 wt % carbon black to the pearlite powder reduces the conductivity of only 15%, which is smaller in effect of improvement of the thermal insulation property than those of the present exemplary embodiments.

(Comparative Sample 2.3)

Core member used for a vacuum thermal insulator here consists of 90 wt % wet silica having an average primary particulate diameter of 20 nm, and 10 wt % carbon black having a specific surface area of 50 m$^2$/g, as the powdery carbon material, which are uniformly mixed in a mixing container equipped with stirring blades. The core member is packed into an enveloping member made of nonwoven fabric of polyester. It is then packed in an enveloping member of laminate enveloping member, which consists of a surface protective layer of polyethylene terephthalate film, a gas barrier layer of aluminum foil, and a heat welding layer of non-oriented polypropylene. Then they are sealed under a pressure of 133 Pa with a thermal welding machine, to obtain the vacuum thermal insulator.

A coefficient of thermal conductivity of this vacuum thermal insulator is 0.0049 kcal/mh° C.

A coefficient of thermal conductivity of another vacuum thermal insulator containing the pearlite powder only is 0.0062 kcal/mh° C. Thus, adding the 10 wt % carbon black to the wet silica reduces the conductivity by only 20%, which is smaller in effect of improvement of the thermal insulation property as compared to those of the present exemplary embodiments.

(Comparative Sample 2.4)

Core member used here consists of 90 wt % fumed silica having an average primary particulate diameter of 7 nm, 9 wt % carbon black having a specific surface area of 50 m$^2$/g, as the powdery carbon material, and 1% of other material, which are mixed and stirred in a mixing container not equipped with stirring blades but only a rotor in the bottom of it. Agglomerates of the fumed silica are produced in the core member because the material is not uniformly mixed. The core member is packed into an enveloping member made of nonwoven fabric of polyester. It is then packed in an enveloping member of laminate enveloping member, which consists of a surface protective layer of polyethylene terephthalate film, a gas barrier layer of ethylene vinyl-alcohol copolymer film provided with metallized aluminum, and a heat welding layer of non-oriented polypropylene. Then they are sealed under a pressure of 133 Pa with a thermal welding machine, to obtain the vacuum thermal insulator.

A coefficient of thermal conductivity of this vacuum thermal insulator is 0.0048 kcal/mh° C.

An effect of improvement in the thermal insulation property is notably reduced, since secondary agglomerates of the fumed silica are not ground and therefore not uniformly mixed with the carbon black.

(Comparative Sample 2.5)

A vacuum thermal insulator described in the comparative sample 2.3 is placed in a notebook type computer as shown in FIG. 15. A temperature on a bottom surface of the computer is decreased only by 2° C. over the one not provided with the thermal insulator, indicating a poorer effect of thermal insulation than that of the embodiment sample 2.8.

(Eighteenth Exemplary Embodiment)

Figure 18:
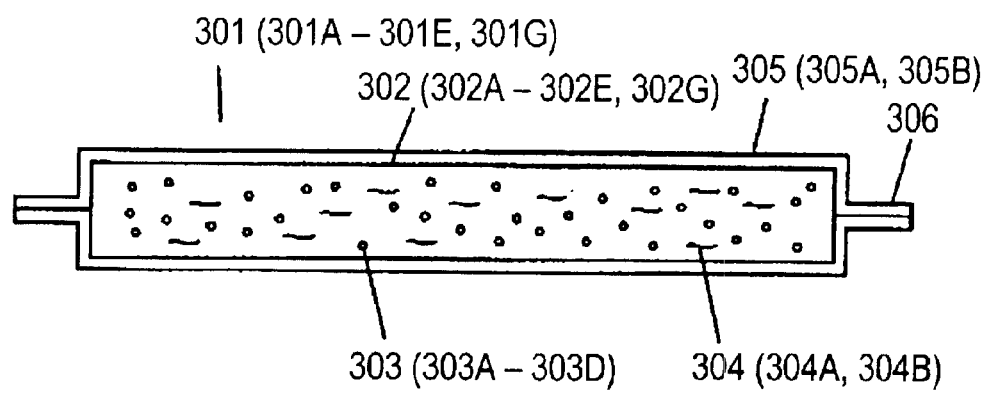
FIG. 18 is a sectional view of a vacuum thermal insulator representing all of eighteenth through twenty-third and twenty-fifth exemplary embodiments of the invention.

FIG. 18 is a sectional view of a vacuum thermal insulator in the eighteenth exemplary embodiment.

Vacuum thermal insulator 301 includes formed body 302 made from mixture of powder 303 and fibrous material 304, and enveloping member 305 for covering the formed body 302. They are sealed with the inside decompressed.

The formed body 302 is formed in a manner that 90 wt % dry silica having an average primary particulate diameter of 7 nm and 10 wt % glass wool with an average fiber diameter of 7 $\mu$m are uniformly mixed in a cutter mill, put in a molding die, and compressed with a pressure of 1.2N/mm$^2$. The formed body 302 had a density of 190 kg/m$^3$ under the atmospheric pressure, and has a coefficient of thermal conductivity of 0.026 W/mK under the atmospheric pressure. A bending strength of the formed body 302 is 0.21 N/mm$^2$.

The formed body 302 is dried for one hour at 110° C., inserted into the enveloping member 305, and an interior of the enveloping member 305 is decompressed to 20 Pa and sealed.

The enveloping member 305 is provided with a surface protective layer of polyethylene terephthalate (12 $\mu$m in thickness), a film layer of ethylene vinyl-alcohol copolymer composite (15 $\mu$m in thickness) with metallized aluminum deposited on an interior side, and a heat seal layer of high density polyethylene (50 $\mu$m in thickness).

The enveloping member 305 is sealed at four sides, which leaves fin 306 around its periphery.

A coefficient of thermal conductivity of the vacuum thermal insulator 301 is 0.0062 W/mK at an average temperature of 24° C.

The formed body has a thickness D301 before being inserted into the enveloping member, and has a thickness D302 after being included in the vacuum thermal insulator. A ratio of change in thickness represented by AT is given as:

$\Delta T=(D302-D301)\times100/D301=2\%$.

Table 301 shows these results.

(Nineteenth Exemplary Embodiment)

FIG. 18 represents a sectional view of a vacuum thermal insulator in the nineteenth exemplary embodiment.

Vacuum thermal insulator 301A includes formed body 302A. The formed body 302A is composed in a manner that powder 303A made of 85.5 wt % dry silica having an average primary particulate diameter of 7 nm mixed with 4.5 wt % carbon black having an average particulate diameter of 42 nm is further mixed with 10 wt % glass wool of 7 $\mu$m in an average fiber diameter as fibrous material 304.

The formed body 302A is so formed that after the powder 303A is mixed in a cutter mil, it is further mixed with the fibrous material 304 added to it, put in a molding die, and compressed with a pressure of 1.2N/mm$^2$. The formed body 302A has a density of 190 kg/m$^3$ under the atmospheric pressure, and has a coefficient of thermal conductivity is 0.022 W/mK under the atmospheric pressure. This is a coefficient of thermal conductivity superior to the static electricity so that this formed body can provide for a good insulating efficiency even if being used under the normal atmosphere instead of making it into a vacuum thermal insulator.

A bending strength of the formed body 302A is 0.21N/mm$^2$.

The formed body 302A is dried for one hour at 110° C., inserted into enveloping member 305, and an interior of it is decompressed to 20 Pa and sealed. The enveloping member 305 is analogous to that of the eighteenth exemplary embodiment.

A coefficient of thermal conductivity of the vacuum thermal insulator 301A is 0.005 W/mK at an average temperature of 24° C.

The formed body has a thickness D301 before being inserted into the enveloping member, and has a thickness D302 after being included in the vacuum thermal insulator. A ratio of change in thickness represented by AT is given as:

$\Delta T=(D302-D301)\times100/D301=2\%$.

Table 301 shows results of the evaluation.

The coefficient of thermal conductivity is substantially reduced by adding the carbon black, as compared with the vacuum thermal insulator 301 described in the eighteenth exemplary embodiment.

(Twentieth Exemplary Embodiment)

FIG. 18 represents a sectional view of a vacuum thermal insulator in the twentieth exemplary embodiment.

Vacuum thermal insulator 301B includes a formed body 302B. The formed body 302B is composed in a manner that powder 303B made of 85.5 wt % dry silica having an average primary particulate diameter of 7 nm mixed with 4.5 wt % titanium oxide having an average particulate diameter of 60 nm is further mixed with 10 wt % glass wool of 7 $\mu$m in an average fiber diameter as fibrous material 304.

The formed body 302B is so formed that after the powder 303B is mixed in a cutter mil, it is further mixed with the fibrous material 304 added to it, put in a molding die, and compressed with a pressure of 1.2N/mm$^2$. The formed body 302B has a density of 180 kg/m$^3$ under the atmospheric pressure, and has a coefficient of thermal conductivity of 0.025 W/mK under the atmospheric pressure.

A bending strength of the formed body 302B is 0.2 N/mm$^2$.

The formed body 302B is dried for one hour at 110° C., inserted into enveloping member 305, and an interior of it is decompressed to 20 Pa and sealed. The enveloping member 305 is analogous to that of the eighteenth exemplary embodiment.

A coefficient of thermal conductivity of the vacuum thermal insulator 301B is 0.0062 W/mK at an average temperature of 24° C.

The formed body has thickness D301 before being inserted into the enveloping member, and has has thickness D302 after being included in the vacuum thermal insulator. A ratio of change in thickness represented by $\Delta$T is given as:

$\Delta T=(D302-D301)\times100/D301=2\%$.

Table 301 shows results of the evaluation.

Although there is no difference in the solidified strength as compared with the vacuum thermal insulator 301 described in the eighteenth exemplary embodiment, there is little effect to a reduction of the coefficient of thermal conductivity by addition of the titanium oxide.

(Twenty-First Exemplary Embodiment)

FIG. 18 is a sectional view of a vacuum thermal insulator in the twenty-first exemplary embodiment.

Vacuum thermal insulator 301C includes a formed body 302C. The formed body 302C is composed by mixing 90 wt % dry silica having an average primary particulate diameter of 7 nm, as powder 303, with 10 wt % glass wool of 0.8 μm in an average fiber diameter, as fibrous material 304A.

The formed body 302C is produced in the same manner as the eighteenth exemplary embodiment. The formed body 302C has a density of 180 kg/m$^3$ under the atmospheric pressure, a coefficient of thermal conductivity of 0.025 W/mK also under the atmospheric pressure, and a bending strength of 0.24N/mm$^2$.

Including the formed body 302C, the vacuum thermal insulator 301C is produced in the same method as the eighteenth exemplary embodiment. The enveloping member 305 is also analogous to that of the eighteenth exemplary embodiment.

A coefficient of thermal conductivity of the vacuum thermal insulator 301C is 0.0057 W/mK at an average temperature of 24° C. It has 1% in ratio of change in the thickness.

Table 301 shows results of the evaluation.

There are improvements for all of the coefficient of thermal conductivity, the bending strength, and the ratio of change in thickness, since fiber diameter of the fibrous material is reduced finely as compared to the vacuum thermal insulator 301 described in the eighteenth exemplary embodiment.

(Twenty-Second Exemplary Embodiment)

FIG. 18 represents a sectional view of a vacuum thermal insulator in the twenty-second exemplary embodiment.

Vacuum thermal insulator 301D includes a formed body 302D. The formed body 302D is composed in a manner that powder 303A made of 85.5 wt % dry silica having an average primary particulate diameter of 7 nm mixed with 4.5 wt % carbon black having an average particulate diameter of 42 nm is further mixed with 10 wt % glass wool 304A of 0.8 μm in an average fiber diameter.

The formed body 302D is produced in the same manner as the nineteenth exemplary embodiment. The formed body 302D has a formed density of 180 kg/m$^3$ under the atmospheric pressure, a coefficient of thermal conductivity of 0.02 W/mK also under the atmospheric pressure, and a bending strength of 0.25N/mm$^2$.

Including the formed body 302D, the vacuum thermal insulator 301D is produced in the same method as the nineteenth exemplary embodiment. The enveloping member 305 is also analogous to that of the nineteenth exemplary embodiment.

A coefficient of thermal conductivity of the vacuum thermal insulator 301D is 0.0044 W/mK at an average temperature of 24° C., and it has 1% in ratio of change in the thickness.

Table 301 shows results of the evaluation.

There are substantial improvements for all of the coefficient of thermal conductivity, the bending strength, and the ratio of change in thickness, since fiber diameter of the fibrous material is reduced finely besides the addition of carbon black, as compared to the vacuum thermal insulator 301 described in the eighteenth exemplary embodiment.

(Twenty-Third Exemplary Embodiment)

FIG. 18 represents a sectional view of a vacuum thermal insulator in the twenty-third exemplary embodiment.

Vacuum thermal insulator 301E includes a formed body 302E. The formed body 302E is composed in a manner that powder 303A made of 85.5 wt % dry silica having an average primary particulate diameter of 7 nm mixed with 4.5 wt % carbon black having an average particulate diameter of 42 nm is further mixed with 10 wt % glass wool, as fibrous material 304A of 0.8 μm in an average fiber diameter.

The formed body 302E is produced in the same manner as the nineteenth exemplary embodiment, except that the compressing pressure is set to 0.4 N/mm$^2$. The formed body 302E has a density of 140 kg/m$^3$ under the atmospheric pressure, a coefficient of thermal conductivity of 0.02 W/mK also under the atmospheric pressure, and a bending strength of 0.14 N/mm$^2$.

Including the formed body 302E, the vacuum thermal insulator 301E is produced in the same method as the nineteenth exemplary embodiment. Enveloping member 305 of the same specification as that of the nineteenth exemplary embodiment is also used.

A coefficient of thermal conductivity of the vacuum thermal insulator 301E is 0.0042 W/mK at an average temperature of 24° C., and it has 3% in ratio of change in the thickness.

Table 301 shows results of the evaluation.

Although there is an improvement in the coefficient of thermal conductivity as a result of reduction of the compression pressure, the bending strength is decreased when compared with the vacuum thermal insulator 301D described in the twenty-second exemplary embodiment.

(Twenty-Fourth Exemplary Embodiment)

Figure 19:
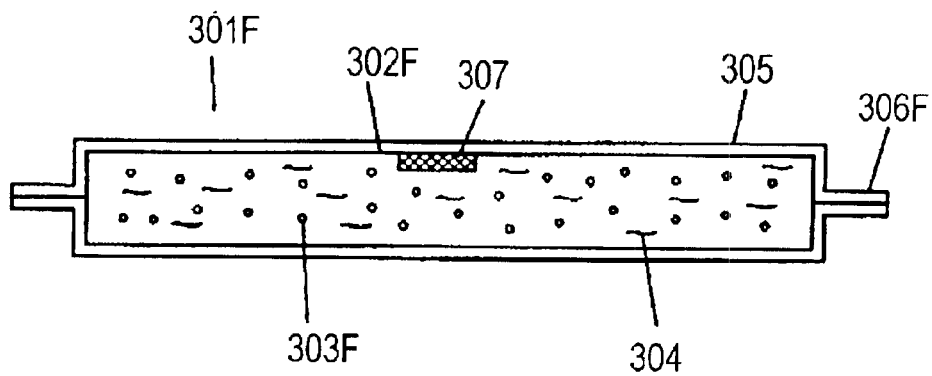
FIG. 19 is a sectional view of a vacuum thermal insulator according to a twenty-fourth exemplary embodiment of the invention.

FIG. 19 is a sectional view of a vacuum thermal insulator in the twenty-fourth exemplary embodiment.

Vacuum thermal insulator 301F includes a formed body 302F. The formed body 302F is composed in a manner that powder 303C made of 85.5 wt % dry silica having an average primary particulate diameter of 56 nm mixed with 9.5 wt % carbon black having an average particulate diameter of 42 nm is further mixed with 5 wt % fibrous material 304 consisting of glass wool having 7 μm in an average fiber diameter.

The formed body 302F is formed in a manner that the dry silica, the carbon black and the glass wool are mixed simultaneously in a cutter mill, put in a molding die, and compressed with a pressure of 1.2N/mm$^2$.

The formed body 302F has a density of 180 kg/m$^3$ under the atmospheric pressure, and has a coefficient of thermal conductivity of 0.021 W/mK also under the atmospheric pressure, and a bending strength of 0.21N/mm$^2$.

The formed body 302F is dried for one hour at 110° C., inserted into enveloping member 305A together with adsorbent 307, and an interior of the enveloping member 305A is decompressed to 20 Pa and sealed.

One side of the enveloping member 305A is formed with a lamination film including an outermost layer of a nylon film (15 μm in thickness), a surface protective layer of polyethylene terephthalate (12 μm in thickness), an intermediate part of aluminum foil (6 μm in thickness), and a heat seal layer of high density polyethylene (50 μm in thickness). The other side is formed also with a lamination film comprising an outermost layer of a nylon film (15 μm in thickness), a surface protective layer of polyethylene terephthalate (12 μm in thickness), an intermediate part of film layer comprised of ethylene vinyl-alcohol copolymer composite (15 μm in thickness) with metallized aluminum deposited on an interior side, and a heat seal layer of high density polyethylene (50 µm in thickness).

The adsorbent 307 is moisture adsorbent composed of granulated calcium oxide placed in an enveloping member having moisture permeability.

The vacuum thermal insulator 301F constructed as above has a coefficient of thermal conductivity of 0.0049 W/mK at an average temperature of 24° C., and a ratio of 1% in change of the thickness.

Table 301 shows results of the evaluation.

Although there is an adverse influence to the coefficient of thermal conductivity of the powder due to the increase in particulate diameter, as compared to the vacuum thermal insulator 301A described in the nineteenth exemplary embodiment, the insulator has an equivalent coefficient of thermal conductivity to that of the vacuum thermal insulator 301A because an added amount of the fibrous material is reduced.

Adding the adsorbent 307 improves reliability over the elapse of time.

(Twenty-Fifth Exemplary Embodiment)

FIG. 18 represents a sectional view of a vacuum thermal insulator in the twenty-fifth exemplary embodiment.

Vacuum thermal insulator 301G includes a formed body 302G. The formed body 302G is composed in a manner that powder 303D made of 64 wt % dry silica having an average primary particulate diameter of 7 nm mixed with 16 wt % carbon black having an average particulate diameter of 30 nm is further mixed with fibrous material 304B made of 10 wt % silica-alumina fiber having an average fiber diameter of 1.1 µm mixed with 10 wt % glass wool having an average fiber diameter of 8 µm.

The formed body 302G is produced in the same manner as the nineteenth exemplary embodiment, except that the compressing pressure is set to 1.5N/mm². The formed body 302G has a density of 200 kg/m³ under the atmospheric pressure, a coefficient of thermal conductivity of 0.022 W/mK also under the atmospheric pressure, and a bending strength of 0.23N/mm².

The formed body 302G is dried for one hour at 110° C., inserted into enveloping member 305B, and an interior of the enveloping member 305B is decompressed to 20 Pa and sealed.

One side of the enveloping member 305B includes an outermost layer of nylon (12 µm in thickness), an intermediate part of film layer made of polyethylene terephthalate (12 µm in thickness) deposited on an inner side with metallized aluminum, another film layer inside of it made of ethylene vinyl-alcohol copolymer film (12 µm in thickness) deposited on an outer surface with metallized aluminum, and a heat seal layer of polypropylene (50 µm in thickness). The other side includes an outermost layer of nylon (12 µm in thickness), a surface protective layer of polyethylene terephthalate (12 µm in thickness), an intermediate part of aluminum foil (6 µm in thickness), and a heat seal layer of polypropylene (50 µm in thickness).

The vacuum thermal insulator 301G has a coefficient of thermal conductivity of 0.0050 W/mK at an average temperature of 24° C., and a ratio of 1% in change of the thickness.

Table 301 shows results of the evaluation.

The fiber is blended in consideration of a balance between a reduction in the coefficient of thermal conductivity due to fining of the fiber diameter and a reduction in cost due to increase of the fiber diameter, upon comparison with the vacuum thermal insulator 301A in the nineteenth exemplary embodiment. An increase of the compression pressure provides the vacuum thermal insulator with outstanding improvement to the bending strength and the ratio of change in thickness, while maintaining the coefficient of thermal conductivity generally unchanged.

TABLE 301

| | Composition of core member | | | | | |
|---|---|---|---|---|---|---|
| | Powder | | | Fiber | | |
| | Dry Silica wt % (particle diameter) | Carbon Black wt % (particle diameter) | Other Material wt % (particle diameter) | Glass wool wt % (fiber diameter) | Silica alumina fiber wt % (fiber dia.) | Compression pressure (N/mm²) |
| 18th exemplary embodiment | 90 wt % (7 nm) | — | — | 10 wt % (7 µm) | — | 1.2 |
| 19th exemplary embodiment | 85.5 wt % (7 nm) | 4.5 wt % (42 nm) | — | 10 wt % (7 µm) | — | 1.2 |
| 20th exemplary embodiment | 85.5 wt % (7 nm) | — | Titanium oxide 4.5 wt % (60 nm) | 10 wt % (7 µm) | — | 1.2 |
| 21st exemplary embodiment | 90 wt % (7 nm) | — | — | 10 wt % (0.8 µm) | — | 1.2 |
| 22nd exemplary embodiment | 85.5 wt % (7 nm) | 4.5 wt % (42 nm) | — | 10 wt % (0.8 µm) | — | 1.2 |
| 23rd exemplary embodiment | 85.5 wt % (7 nm) | 4.5 wt % (42 nm) | — | 10 wt % (0.8 µm) | — | 0.4 |
| 24th exemplary embodiment | 85.5 wt % (7 nm) | 9.5 wt % (42 nm) | — | 5 wt % (7 µm) | — | 1.2 |
| 25th exemplary embodiment | 64 wt % (7 nm) | 16 wt % (30 nm) | — | 10 wt % (8 µm) | 10 wt % (1.1 µm) | 1.2 |

| | Characteristics of core member and vacuum thermal insulator | | | |
|---|---|---|---|---|
| | Coefficient of thermal conductivity (W/mK) | Density (kg/m³) | Bending strength (N/mm²) | Ratio of change in thickness (%) |
| 18th exemplary embodiment | Normal pressure, 20 Pa | 0.026 0.0062 | 190 | 0.21 | 2 |
| 19th exemplary embodiment | Normal pressure, 20 Pa | 0.0022 0.005 | 190 | 0.21 | 2 |
| 20th exemplary embodiment | Normal pressure, 20 Pa | 0.0025 0.0062 | 180 | 0.2 | 2 |
| 21st exemplary embodiment | Normal pressure, 20 Pa | 0.025 0.0057 | 180 | 0.24 | 1 |
| 22nd exemplary embodiment | Normal pressure, 20 Pa | 0.02 0.0044 | 180 | 0.25 | 1 |
| 23rd exemplary embodiment | Normal pressure, 20 Pa | 0.02 0.0042 | 140 | 0.14 | 3 |
| 24th exemplary embodiment | Normal pressure, 20 Pa | 0.021 0.0049 | 180 | 0.21 | 1 |
| 25th | Normal | 0.22 | 200 | 0.23 | 1 |

TABLE 301-continued

| exemplary embodiment | pressure, 20 Pa | 0.005 |

(Twenty-Sixth Exemplary Embodiment)

Figure 20:
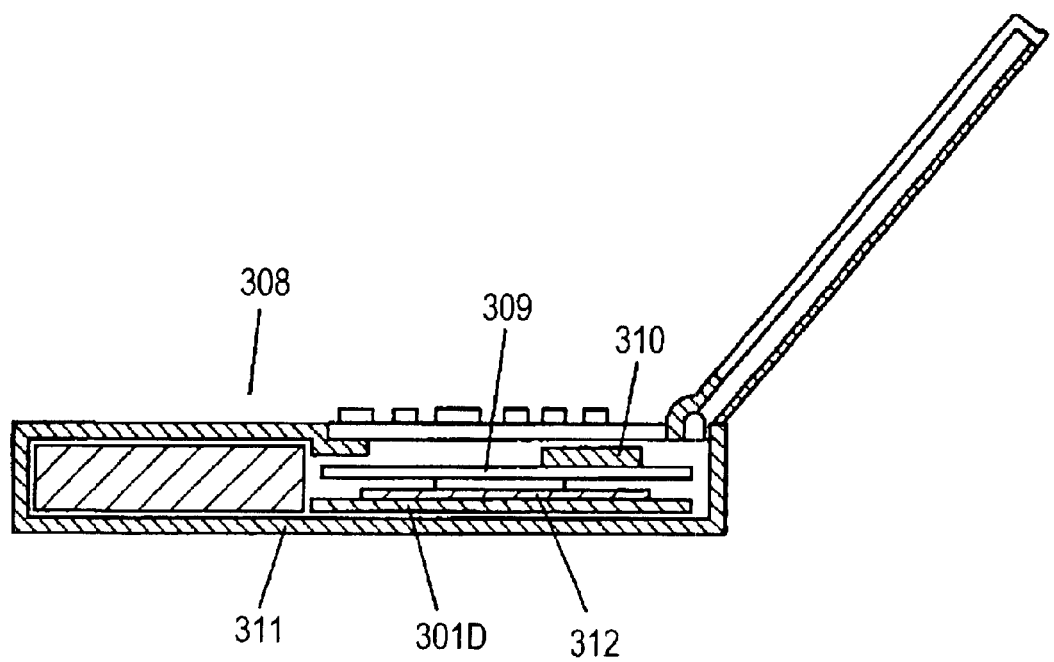
FIG. 20 is a sectional view of a notebook type computer according to a twenty-sixth exemplary embodiment of the invention.

FIG. 20 is a sectional view of a notebook type computer according to the 6 twenty-sixth exemplary embodiment.

The notebook type computer 308 is provided with vacuum thermal insulator 301D and heat sink 312, which shield between heating component 310 on main board 309 in the device and a bottom of device enclosure 311.

Materials of the vacuum thermal insulator 301D and method of producing it are similar to those stated in the twenty-second exemplary embodiment. Dimensions of a formed body in the vacuum thermal insulator 301D are 60 mm by 60 mm by 1 mm. Fin 306 of the enveloping member 305 left around the vacuum thermal insulator 301D is folded, and the heat sink 12 is placed on a surface to which the fin 306 is folded.

A temperature on the bottom surface of the notebook type computer 808 is lower by 5° C. than that of the notebook type computer not provided with a vacuum thermal insulator. In addition, there is no verifiable deterioration in the thermal insulation property under the condition of a ten-year duration according to an accelerated test.

(Comparative Sample 3.1)

Figure 21:
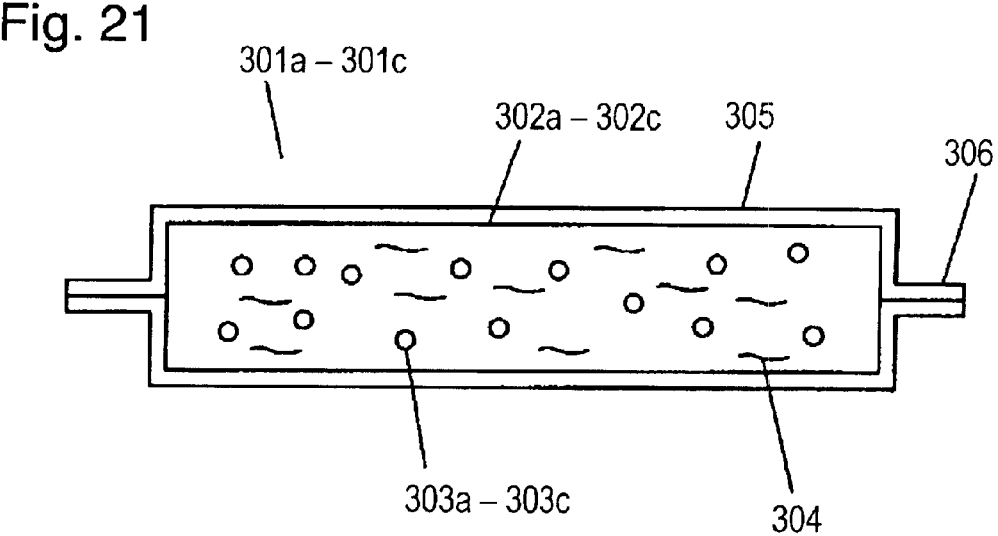
FIG. 21 is a sectional view of a vacuum thermal insulator of comparative samples 3.1 to 3.3.

FIG. 21 is a sectional view of a vacuum thermal insulator of the comparative sample 3.1.

Vacuum thermal insulator 301a has formed body 302a containing mixture of powder 303a and fibrous material 304. The formed body 302a is inserted in the enveloping member 305, and an interior of the enveloping member 305 is decompressed and sealed.

The formed body 302a is formed in a manner that 90 wt % dry silica having an average secondary particulate diameter of 150 nm as powder 303a and 10 wt % glass wool having an average fiber diameter of 7 μm as fibrous material 304 are uniformly mixed in a cutter mill, are put into a molding die, and are compressed with a pressure of 1.2N/mm$^2$.

The formed body 302a is very brittle that it crumbles partially when picked up with a hand, and it also raises heavy powdery dust.

The formed body 302a has a density of 250 kg/m$^3$ under the atmospheric pressure, a coefficient of thermal conductivity of 0.032 W/mK under the atmospheric pressure, and a bending strength of 0.03N/mm$^2$.

The formed body 302a is dried for one hour at 110° C., and inserted carefully into the enveloping member 305 while being carried on a plastic board. After the plastic board is removed, inside of the enveloping member 305 is decompressed to 20 Pa, and sealed. The enveloping member 305 is analogous to that of the eighteenth exemplary embodiment.

The vacuum thermal insulator 301a has a coefficient of thermal conductivity of 0.0068 W/mK at an average temperature of 24° C. and a ratio of 7% in change of the thickness, and the insulator has a rough surface.

Accordingly, it is not adaptable to any devices such as personal computers that require a low-profile vacuum thermal insulator.

Table 302 shows results of the evaluation of the vacuum thermal insulator 301a.

Since the insulator includes the powder of large particulate diameter as compared to the vacuum thermal insulator described in the eighteenth exemplary embodiment, the formed body is not obtained easily, and has a small bending strength.

(Comparative Sample 3.2)

FIG. 21 represents a sectional view of a vacuum thermal insulator of the comparative sample 3.2.

Vacuum thermal insulator 301b is provided with formed body 302b. The formed body 302b is composed through that powder 303b made of 85.5 wt % wet silica having an average primary particulate diameter of 120 nm mixed with 4.5 wt % carbon black having an average particulate diameter of 42 nm is further mixed with 10 wt % glass wool of 7 μm in an average fiber diameter as fibrous material 304.

The formed body 302b is formed in a manner that after the powder 303b is mixed in a cutter mil, it is further mixed with the fibrous material 304 added to it, is put in a molding die, and is compressed with a pressure of 1.2N/mm$^2$.

The formed body 302b is very brittle that it crumbles partially when picked up with a hand and it also raises heavy powdery dust.

The formed body 302b has a density of 250 kg/m$^3$ under the atmospheric pressure, a coefficient of thermal conductivity of 0.028 W/mK under the atmospheric pressure, and a bending strength of 0.03 N/mm$^2$.

The formed body 302b is dried for one hour at 110° C., and inserted carefully into the enveloping member 305 while being carried on a plastic board. After the plastic board is removed, inside of the enveloping member 305 is decompressed to 20 Pa, and sealed. The enveloping member 305 is analogous to that of the eighteenth exemplary embodiment.

The vacuum thermal insulator 301b has a coefficient of thermal conductivity of 0.0053 W/mK at an average temperature of 24° C., a ratio of 7% in change of the thickness, and it has a rough surface.

Table 302 shows results of the evaluation.

Since the insulator uses the powder of large particulate diameter as compared to the vacuum thermal insulator 301A of the nineteenth exemplary embodiment, the formed body is not obtained easily, and it has a small bending strength.

(Comparative Sample 3.3)

FIG. 21 represents a sectional view of a vacuum thermal insulator of the comparative sample 3.3.

Vacuum thermal insulator 301c is provided with formed body 302c. The formed body 302c is composed through that powder 303c made of 45 wt % dry silica having an average primary particulate diameter of 7 nm mixed with 45 wt % wet silica having an average primary particulate diameter of 130 nm is further mixed with 10 wt % glass wool as fibrous material 304 of 7 μm in an average fiber diameter.

The formed body 302c is formed in a manner that after the powder 303c is mixed in a cutter mil, it is further mixed with the fibrous material 304 added to it, is put in a molding die, and is compressed with a pressure of 1N/mm$^2$.

The formed body 302c is very brittle that it crumbles partially when picked up with a hand, and it also raises heavy powdery dust.

The formed body 302c has a density of 230 kg/m$^3$ under the atmospheric pressure, a coefficient of thermal conductivity of 0.028 W/mK under the atmospheric pressure, and a bending strength of 0.05N/mm$^2$.

The formed body 302c is dried for one hour at 110° C., and inserted carefully into the enveloping member 305 while being carried on a plastic board. After the plastic board is removed, inside of the enveloping member 305 is decompressed to 20 Pa, and sealed. The enveloping member 305 is analogous to that of the eighteenth exemplary embodiment.

The vacuum thermal insulator 301c has a coefficient of thermal conductivity of 0.0064 W/mK at an average temperature of 24° C., a ratio of 6% in change of the thickness, and it has a rough surface.

Table 302 shows results of the evaluation.

Since it is blended with the wet silica of large particulate diameter as compared to the vacuum thermal insulator 301 described in the eighteenth exemplary embodiment, the formed body is not obtained easily, and it has a small bending strength.

TABLE 302

| | Composition of core member | | | | |
|---|---|---|---|---|---|
| | Powder | | | | |
| | Dry silica wt % (particulate diameter) | Wet silica Wt % (particulate diameter) | Carbon black, wt % (particulate diameter) | Fiber Glass wool wt % (fiber diameter) | Compression pressure (N/mm²) |
| Comparative sample 3.1 | 90 wt % (150 nm) | — | — | 10 wt % (7 μm) | 1.2 |
| Comparative sample 3.2 | — | 85.5 wt % (120 nm) | 4.5 wt % (42 nm) | 10 wt % (7 μm) | 1.2 |
| Comparative sample 3.3 | 45 wt % (7 nm) | 45 wt % (130 nm) | — | 10 wt % (7 μm) | 1 |

| | Characteristics of core member and vacuum thermal insulator | | | |
|---|---|---|---|---|
| | Coefficient of thermal conductivity (W/mK) | Density (kg/mm³) | Bending strength (N/mm²) | Ratio of change in thickness (%) |
| Comparative sample 3.1 | Normal pressure, 20 Pa | 0.032 0.0068 | 250 | 0.03 | 7 |
| Comparative sample 3.2 | Normal pressure, 20 Pa | 0.028 0.0053 | 250 | 0.03 | 7 |
| Comparative sample 3.3 | Normal pressure, 20 Pa | 0.028 0.0064 | 230 | 0.05 | 6 |

INDUSTRIAL APPLICABILITY

According to the invention, a portable information device such as a low-profile notebook type computer is provided which has a highly efficient thermal insulator capable of blocking a transfer of heat between an internal heating component and a device enclosure so as to reduce temperature rise on a surface of the device. A portable information device is further provided which has an efficient thermal insulator for blocking a transfer of heat between the heating component and an expansion unit mounting case, thereby alleviating malfunction and temperature rise of the external expansion unit.

What is claimed is:

1. A portable information device comprising:
   an enclosure;
   a heating component placed in said enclosure; and
   a vacuum thermal insulator placed between said enclosure and said heating component.

2. The portable information device as set forth in claim 1, further comprising a heat sink placed within said enclosure, for dissipating heat generated by said heating component.

3. The portable information device as set forth in claim 1, wherein said thermal insulator has a thickness of 5 mm or less.

4. The portable information device as set forth in claim 1, wherein said vacuum thermal insulator includes a core member having inorganic powder.

5. The portable information device as set forth in claim 1, wherein said vacuum thermal insulator includes a core member having inorganic fiber.

6. The portable information device as set forth in claim 1, wherein said vacuum thermal insulator includes a core member having inorganic powder and inorganic fiber.

7. The portable information device as set forth in claim 1, wherein said vacuum thermal insulator includes:
   a core member having fumed silica containing at least 1 wt % or more of powdery carbon; and
   an enveloping member for enclosing said core member.

8. The portable information device as set forth in claim 7, wherein said fumed silica has an average primary particulate diameter of 50 nm or less.

9. The portable information device as set forth in claim 7, wherein said powdery carbon includes carbon black of a specific surface area smaller than 100 m²/g.

10. The portable information device as set forth in claim 7,
   wherein said fumed silica contains said powdery carbon in an amount of 30 wt % or less, and
   wherein said powdery carbon includes carbon black of a specific surface area smaller than 300 m²/g, but not smaller than 100 m²/g.

11. The portable information device as set forth in claim 7, wherein said powdery carbon includes graphitized carbon powder.

12. The portable information device as set forth in claim 7 further comprising a nonwoven fabric placed between said core member and said enveloping member, for covering said core member.

13. The portable information device as set forth in claim 7, wherein said enveloping member includes a metallized film layer and a thermoplastic polymer layer.

14. The portable information device as set forth in claim 1, wherein said vacuum thermal insulator includes:
   a formed body containing dry silica having an average primary particulate diameter of 100 nm or less and fibrous material having an average fiber diameter of 10 μm or less; and
   an enveloping member having gas barrier property.

15. The portable information device as set forth in claim 14, wherein said formed body further contains powdery carbon.

16. A portable information device comprising:
   an enclosure;
   a heating component placed in said enclosure;
   an expansion unit mounting case placed in said enclosure; and
   a vacuum thermal insulator placed between said heating component and said expansion unit mounting case.

17. The portable information device as set forth in claim 16, wherein said thermal insulator has a thickness of 5 mm or less.

18. The portable information device as set forth in claim 16, wherein said vacuum thermal insulator includes a core member having inorganic powder.

19. The portable information device as set forth in claim 16, wherein said vacuum thermal insulator includes a core member having inorganic fiber.

20. The portable information device as set forth in claim 16, wherein said vacuum thermal insulator includes a core member having inorganic powder and inorganic fiber.

21. The portable information device as set forth in claim 16, wherein said vacuum thermal insulator includes:
   a core member having fumed silica containing at least 1 wt % or more of powdery carbon; and
   an enveloping member for enclosing said core member.

22. The portable information device as set forth in claim 16, wherein said vacuum thermal insulator includes:
   a formed body containing dry silica having an average primary particulate diameter of 100 nm or less and fibrous material having an average fiber diameter of 10 μm or less; and
   an enveloping member having gas barrier property.

23. A portable information device comprising:
   an enclosure;
   a heating component placed in said enclosure; and
   an expansion unit mounting case placed within said enclosure, said expansion unit mounting case including a vacuum thermal insulator.

24. The portable information device as set forth in claim 23, wherein said thermal insulator has a thickness of 5 mm or less.

25. A portable information device comprising:
   an enclosure;
   a heating component placed in said enclosure; and
   a thermal insulator placed between said enclosure and said heating component, said thermal insulator including a microporous body containing inorganic oxide aerogel in monolith form having a thickness not more than 5 mm.

* * * * *